US010448645B2

(12) United States Patent
Breakfield et al.

(10) Patent No.: US 10,448,645 B2
(45) Date of Patent: Oct. 22, 2019

(54) METHODS AND COMPOSITIONS FOR CONTROLLING ROOT LESION NEMATODES

(71) Applicant: NewLeaf Symbiotics, Inc., St. Louis, MO (US)

(72) Inventors: Natalie Breakfield, St. Louis, MO (US); Gregg Bogosian, Clarkson Valley, MO (US)

(73) Assignee: NewLeaf Symbiotics, Inc., St. Louis, MO (US)

(*) Notice: Subject to any disclaimer, the term of this patent is extended or adjusted under 35 U.S.C. 154(b) by 3 days.

(21) Appl. No.: 15/373,203

(22) Filed: Dec. 8, 2016

(65) Prior Publication Data
US 2017/0164618 A1 Jun. 15, 2017

Related U.S. Application Data

(60) Provisional application No. 62/266,115, filed on Dec. 11, 2015.

(51) Int. Cl.
*A01N 63/00* (2006.01)

(52) U.S. Cl.
CPC .................................. *A01N 63/00* (2013.01)

(58) Field of Classification Search
CPC ..................... A01N 63/00; C12N 15/8285
See application file for complete search history.

(56) References Cited

U.S. PATENT DOCUMENTS

| | | | |
|---|---|---|---|
| 5,106,648 A | 4/1992 | Williams | |
| 5,512,069 A | 4/1996 | Holland et al. | |
| 5,549,889 A * | 8/1996 | Zuckerman | A01N 63/00 424/93.43 |
| 5,961,687 A | 10/1999 | Joshi et al. | |
| 6,174,837 B1 | 1/2001 | Joshi et al. | |
| 6,329,320 B1 | 12/2001 | Joshi et al. | |
| 7,435,878 B2 | 10/2008 | Holland | |
| 8,153,118 B2 | 4/2012 | Holland et al. | |
| 8,181,388 B2 | 5/2012 | Berger | |
| 9,181,541 B2 | 11/2015 | Bogosian | |
| 9,845,462 B2 | 12/2017 | Bogosian | |
| 10,098,353 B2 | 10/2018 | Breakfield et al. | |
| 10,111,438 B2 | 10/2018 | Floro et al. | |
| 2001/0001095 A1 | 5/2001 | Joshi et al. | |
| 2015/0337256 A1 | 11/2015 | Bogosian | |
| 2016/0046925 A1 | 2/2016 | Bogosian | |
| 2016/0073641 A1 | 3/2016 | Allen et al. | |
| 2016/0120188 A1 | 5/2016 | Bogosian | |
| 2016/0295868 A1 | 10/2016 | Jones et al. | |
| 2016/0302423 A1 | 10/2016 | Jones et al. | |
| 2016/0302424 A1 | 10/2016 | DiDonato et al. | |
| 2016/0302425 A1 | 10/2016 | DiDonato et al. | |
| 2017/0086464 A1 | 3/2017 | Floro et al. | |
| 2017/0135352 A1 | 5/2017 | Breakfield et al. | |
| 2017/0238553 A1 | 8/2017 | Jones et al. | |
| 2018/0142230 A1 | 5/2018 | Bogosian | |
| 2018/0295841 A1 | 10/2018 | Rioux | |

FOREIGN PATENT DOCUMENTS

| | | | | |
|---|---|---|---|---|
| WO | 2012/140212 A2 | 10/2012 | | |
| WO | WO-2012140212 A2 * | 10/2012 | ............. | A01N 63/00 |
| WO | 2013/181610 A1 | 12/2013 | | |
| WO | 2014194189 A1 | 12/2014 | | |
| WO | 2015/085063 A1 | 6/2015 | | |
| WO | 2015142393 A1 | 9/2015 | | |
| WO | 2016069564 A1 | 5/2016 | | |
| WO | 2016201284 A2 | 12/2016 | | |
| WO | 2018106899 A1 | 6/2018 | | |

OTHER PUBLICATIONS

Knief, Claudia, et al. "Cultivation-independent characterization of Methylobacterium populations in the plant phyllosphere by automated ribosomal intergenic spacer analysis." Applied and environmental microbiology 74.7 (2008): 2218-2228 (Year: 2008).*
Prabhu, S., et al. "Suppressive effect of Methylobacterium fujisawaense against root-knot nematode, Meloidogyne incognita." Indian Journal of Nematology 39.2 (2009): 165. (Year: 2009).*
"ATCC Bacteria and Bacteriophages", American Type Culture Collection, 1996, pp. 213-214, 19th Edition.
"ATCC Preservation Methods: Freezing and Freeze-Drying", 1991, pp. 5-13, 2nd Edition, ATCC.
Abanda-Nkpwatt et al., "Molecular Interaction Between Methylobacterium Extorquens and Seedlings: Growth Promotion, Methanol Consumption, and Localization of the Methanol Emission Site", Journal of Experimental Botany, Oct. 16, 2006, vol. 57 No. 15, pp. 4025-4032.
Corpe et al., "Ecology of the Methylotrophic Bacteria on Living Leaf Surfaces", FEMS Microbiology Ecology, 1989, vol. 62, pp. 243-250.
Green, "Methylobacterium", Prokaryotes, 2006, vol. 5, Chapter 3.1.13, pp. 257-265.
Holland, "Methylobacterium and Plants", Recent Research Developments in Plant Physiology, 1997, pp. 207-213, vol. 1.
Joe et al., "Development of Alginate-Based Aggregate Inoculants of Methylobacterium sp. and Azospirillum Brasilence Tested Under In Vitro Conditions to Promote Plant Growth", Journal of Applied Microbiology, Nov. 22, 2013, pp. 408-423, vol. 116, Issue 2.
Lidstrom et al., "Plants in the Pink: Cytokinin Production by Methylbacterium", Journal of Bacteriology, Apr. 2002, p. 1818, vol. 184, No. 7.

(Continued)

Primary Examiner — Weihua Fan
(74) Attorney, Agent, or Firm — Thompson Coburn LLP; Charles P. Romano

(57) ABSTRACT

The present disclosure provides compositions comprising Root-Lesion Nematode (RLN)-inhibitory *Methylobacterium* sp., as well as cell-free culture supernatants, fractions, and concentrates obtained from the Root-Lesion Nematode (RLN)-inhibitory *Methylobacterium* sp. Also provided are related methods for controlling RLN infections of plants, and methods of making the compositions.

20 Claims, No Drawings
Specification includes a Sequence Listing.

(56) References Cited

OTHER PUBLICATIONS

Madhaiyan et al., "Growth promotion and induction of systemic resistance in rice cultivar Co-47 (*Oryza sativa* L.) *Methylobacterium* spp.", Biology and Fertility of Soils, 2005, pp. 350-358, vol. 41.

Madhaiyan et al., "Metal Tolerating Methylotrophic Bacteria Reduces Nickel and Cadmium Toxicity and Promotes Plant Growth of Tomato (*Lycopersicon esculentum* L.)", Chemosphere, May 23, 2007, pp. 220-228, vol. 69.

Madhaiyan et al., "Pink-Pigmented Facultative Methylotrophic Bacteria Accelerate Germination, Growth and Yield of Sugarcane Clone Co86032 (*Saccharum officinarum* L)", Biology and Fertility of Soils, 2005, pp. 350-358, vol. 41.

Omer et al., "Plant Colonization by Pink-Pigmented Facultative Methylotrophic Bacteria (PPFMs)", FEMS Microbiology Ecology, Mar. 2004, pp. 319-326, vol. 47 No. 3.

Rastogi et al., "Leaf Microbiota in an Agroecosystem Spatiotemporal Variation in Bacterial Community Composition on Field-Grown Lettuce", The ISME Journal, Apr. 26, 2012. pp. 1812-1822, vol. 6.

Sy, A. et al., "Methylotrophic Metabolism Is Advantageous for Methylobacterium extorquens during Colonization of Medicago truncatula under Competitive Conditions", Applied and Environmental Microbiology, 2005, pp. 7245-7252, vol. 71, No. 11.

Vaidehi et al., "Adhesion of Methylobacterium Cells to Rice Roots: Active Metabolism of Miropartner Determines the Degree of Adsorption Level at Rhizosphere", International Journal of Research in Pure and Applied Microbiology, 2012, pp. 54-58, vol. 2, No. 4.

Wessman et al., "Impact of Matrix Properties on the Survival of Freeze-Dried Bacteria", Journal of the Science and Food Agriculture, 2011, pp. 2518-2528, vol. 91.

\* cited by examiner

METHODS AND COMPOSITIONS FOR CONTROLLING ROOT LESION NEMATODES

CROSS-REFERENCE TO RELATED APPLICATIONS

This U.S. non-provisional patent application claims the benefit of U.S. provisional patent application Ser. No. 62/266,115, filed Dec. 11, 2015 and incorporated herein by reference in its entirety

SEQUENCE LISTING STATEMENT

A sequence listing containing the file named 53907_160860_SEQ_LST_ST25.txt which is 14,455 bytes (measured in MS-Windows®) and created on Dec. 1, 2016, comprises 7 sequences, is provided herewith via the USPTO's EFS system, and is incorporated herein by reference in its entirety.

BACKGROUND

One-carbon organic compounds such as methane and methanol are found extensively in nature, and are utilized as carbon sources by bacteria classified as methanotrophs and methylotrophs. Methanotrophic bacteria include species in the genera *Methylobacter, Methylomonas, Methylomicrobium, Methylococcus, Methylosinus, Methylocystis, Methylosphaera, Methylocaldum*, and *Methylocella* (Lidstrom, 2006). Methanotrophs possess the enzyme methane monooxygenase, that incorporates an atom of oxygen from $O_2$ into methane, forming methanol. All methanotrophs are obligate one-carbon utilizers that are unable to use compounds containing carbon-carbon bonds. Methylotrophs, on the other hand, can also utilize more complex organic compounds, such as organic acids, higher alcohols, sugars, and the like. Thus, methylotrophic bacteria are facultative methylotrophs. Methylotrophic bacteria include species in the genera *Methylobacterium, Hyphomicrobium, Methylophilus, Methylobacillus, Methylophaga, Aminobacter, Methylorhabdus, Methylopila, Methylosulfonomonas, Marinosulfonomonas, Paracoccus, Xanthobacter, Ancylobacter* (also known as *Microcyclus*), *Thiobacillus, Rhodopseudomonas, Rhodobacter, Acetobacter, Bacillus, Mycobacterium, Arthobacter*, and *Nocardia* (Lidstrom, 2006).

Most methylotrophic bacteria of the genus *Methylobacterium* are pink-pigmented. They are conventionally referred to as PPFM bacteria, being pink-pigmented facultative methylotrophs. Green (2005, 2006) identified twelve validated species in the genus *Methylobacterium*, specifically *M. aminovorans, M. chloromethanicum, M. dichloromethanicum, M. extorquens, M. fujisawaense, M. mesophilicum, M. organophilum, M. radiotolerans, M. rhodesianum, M. rhodinum, M. thiocyanatum*, and *M. zatmanii*. However, *M. nidulans* is a nitrogen-fixing *Methylobacterium* that is not a PPFM. (Sy et al., 2001). *Methylobacterium* are ubiquitous in nature, being found in soil, dust, fresh water, sediments, and leaf surfaces, as well as in industrial and clinical environments (Green, 2006).

SUMMARY

Provided herein are isolated Root Lesion Nematode (RLN)-inhibitory *Methylobacterium* sp., compositions comprising RLN-inhibitory *Methylobacterium* sp. and/or RLN-inhibitory cell-free culture supernatants, fractions, or concentrates obtained therefrom, methods of using the compositions to control RLN damage to plants, plant parts, and plants derived therefrom, methods of using the compositions to reduce populations of RLN in soil, and methods of making the compositions. Such RLN-inhibitory *Methylobacterium* sp. are in certain instances referred to herein as simply "*Methylobacterium*" or as "PPFM" (pink-pigmented facultative methylotrophs). In certain embodiments, the RLN-inhibitory *Methylobacterium* sp. is a *Methylobacterium* isolate selected from the group consisting of *Methylobacterium* NLS0021, NLS0038, NLS0042, NLS0934, NLS0062, NLS0069, NLS0089, derivatives thereof, and *Methylobacterium* related thereto.

Methods for reducing *Pratylenchus* sp. damage to a plant that comprise applying a composition comprising at least one of a *Methylobacterium* selected from the group consisting of NLS0021, NLS0038, NLS0042, NLS0934, NLS0062, NLS0069, NLS0089, derivatives thereof, *Methylobacterium* related thereto, a RLN-inhibitory cell-free culture supernatant, fraction thereof, concentrate thereof obtained therefrom, and any combination thereof and an agriculturally acceptable excipient and/or an agriculturally acceptable adjuvant to a plant part to obtain a treated plant part; and growing the plant from said treated plant part in the presence of *Pratylenchus* sp., wherein *Pratylenchus* sp. damage to the plant is reduced in comparison to a control plant from a control plant part that is not treated with the *Methylobacterium* and that is grown in the presence of *Pratylenchus* sp. are provided. Such methods may also be used for reducing the populations of RLN in soil. In certain embodiments, the *Methylobacterium* is present on said treated plant part in an amount of at least about $1 \times 10^2$ or $1 \times 10^3$ colony forming units (CFU) of said *Methylobacterium* per treated plant part. In certain embodiments, about $1 \times 10^2$, $1 \times 10^3$, or $1 \times 10^4$ CFU to about $1 \times 10^8$ or $1 \times 10^9$ CFU of the RLN-inhibitory *Methylobacterium* sp. are provided on a 100 mm$^2$ surface of a treated plant part. In certain embodiments of the methods, the composition comprises a solid substance with adherent RLN-inhibitory *Methylobacterium* grown thereon or an emulsion having RLN-inhibitory *Methylobacterium* grown therein. In certain embodiments of the methods, the composition comprises the RLN-inhibitory *Methylobacterium* sp. at a titer of about $1 \times 10^4$ or $1 \times 10^5$ colony-forming units per ml to about $1 \times 10^9$, $1 \times 10^{10}$, $6 \times 10^{10}$, $1 \times 10^{11}$, $5 \times 10^{11}$, or $1 \times 10^{12}$ colony-forming units of *Methylobacterium* per mL of a liquid or emulsion. In certain embodiments of the methods, the composition comprises the RLN-inhibitory *Methylobacterium* sp. at a titer of about $5 \times 10^8$, $1 \times 10^9$, or $1 \times 10^{10}$ colony-forming units per gram (CFU/gm) to about $1 \times 10^{12}$ or $5 \times 10^{13}$ colony-forming units of *Methylobacterium* per gram of a solid substance to which the *Methylobacterium* is adhered or at a titer of about $1 \times 10^6$ CFU/mL to about $1 \times 10^9$ CFU/mL of the *Methylobacterium* in an emulsion. In certain embodiments, the NLS0021, NLS0038, NLS0042, NLS0934, NLS0062, NLS0069, or NLS0089 derivative is obtained by mutagenizing or transforming *Methylobacterium* NLS0021, NLS0038, NLS0042, NLS0934, NLS0062, NLS0069, or NLS0089, respectively. In certain embodiments, the NLS0021, NLS0038, NLS0042, NLS0934, NLS0062, NLS0069, or NLS0089-related *Methylobacterium* is characterized by having a gene encoding a 16S RNA that has at least 95%, 96%, 97%, 98%, 99%, 99.5%, 99.7%, 99.9%, or 100% sequence identity across the entire length of SEQ ID NO: 1, 2, 3, 4, 5, 6, or 7, respectively. In certain embodiments of any of the aforementioned methods, the *Methylobacterium* is heterologous to the plant part. In certain embodiments of any of the aforementioned methods, the *Methylobacterium* is: (i) NLS0021 and the plant part is not a lettuce plant part; (ii) NLS0038 and the plant part is not a tomato plant part; (iii) NLS0042 or NLS0934 and the plant part is not a soybean plant part; (iv) NLS0062 or NLS0069 and the plant part is not a corn plant part; or (v) NLS0089 and the plant part is not a broccoli plant part. In certain embodiments of any of the aforementioned methods, the *Pratylenchus* sp. damage is selected from the group consisting of a reduction in plant growth, yield, water-deficit tolerance, chlorosis, produce quality, and combinations thereof. In certain embodiments of the aforementioned methods, the reduction in damage is evidenced by an increase in shoot weight, root weight, or the combination thereof in the plant in comparison to the control plant. In certain embodiments, such produce is a plant part. In certain embodiments of any of the aforementioned methods, the plant part is a seed, leaf, tuber, or root. In certain embodiments of any of the aforementioned methods, the applied composition coats or partially coats the plant part. In certain embodiments of the aforementioned methods, the composition is applied to the seed. In certain embodiments of any of the aforementioned methods, the *Pratylenchus* sp. is selected from the group consisting of *Pratylenchus brachyurus, Pratylenchus coffeae, P. neglectus Pratylenchus penetrans, Pratylenchus scribneri, Pratylenchus thornei, Pratylenchus vulnus*, and *Pratylenchus zeae*. In certain embodiments of any of the aforementioned methods, the plant part is selected from the group consisting of a *Brassica* sp. corn, wheat, rye, rice, alfalfa, rice, rye, sorghum, millet, soybean, tobacco, potato, peanut, carrot, cotton, coffee, coconut, pineapple, sugar beet, strawberry, oat, barley, tomato, lettuce, pepper, pea, onion, green bean, and cucurbit plant part. In certain embodiments of any of the aforementioned methods, the composition further comprises a nematicide that provides for inhibition of RLN growth, motility, and/or reproduction and/or reductions in RLN-mediated plant damage. In certain embodiments where the composition further comprises a nematicide, the nematicide is selected from the group consisting of an organophosphate, biological, and a carbamate nematicide. In certain embodiments of any of the aforementioned methods, soil in which the plant is to be grown is surveyed for the presence of *Pratylenchus* sp. and the composition is applied to the plant part when *Pratylenchus* sp. are present in the soil at a level that can result in reductions in plant growth, yield, water-deficit tolerance, chlorosis, produce quality, and combinations thereof to an untreated control plant. In certain embodiments of the methods, the composition is not applied to the plant part when the *Pratylenchus* sp. are present in the soil below levels that result in reductions in plant growth, yield, water-deficit tolerance, chlorosis, produce quality, and combinations thereof to an untreated control plant.

Plant parts that are at least partially coated with a composition comprising at least one of a *Methylobacterium* selected from the group consisting of *Methylobacterium* NLS0021, NLS0038, NLS0042, NLS0934, NLS0062, NLS0069, NLS0089, derivatives thereof, *Methylobacterium* related thereto, a RLN-inhibitory cell-free culture supernatant, fraction thereof, concentrate thereof obtained therefrom, and any combination thereof and an agriculturally acceptable excipient and/or an agriculturally acceptable adjuvant, wherein said composition is provided on said plant part in an amount that reduces *Pratylenchus* sp. damage to a plant grown from the plant part in comparison to a control plant grown from a control plant part that is not treated with the *Methylobacterium* are also provided. In certain embodiments, the amount of *Methylobacterium* present on said plant part is at least about $1\times10^3$ colony forming units (CFU) of said *Methylobacterium* per plant part. In certain embodiments, about $1\times10^2$, $1\times10^3$, or $1\times10^4$ CFU to about $1\times10^8$ or $1\times10^9$ CFU of the RLN-inhibitory *Methylobacterium* sp. are provided on a 100 mm$^2$ surface of the plant part. In certain embodiments, about $1\times10^2$, $1\times10^3$, or $1\times10^4$ CFU to about $1\times10^8$ or $1\times10^9$ CFU of the RLN-inhibitory *Methylobacterium* sp. are provided on the surface of a plant part that is a seed. In certain embodiments, the plant part is a seed, leaf, stem, root, or tuber. In certain embodiments, the NLS0021, NLS0038, NLS0042, NLS0934, NLS0062, NLS0069, or NLS0089 derivative is obtained by mutagenizing or transforming *Methylobacterium* NLS0021, NLS0038, NLS0042, NLS0934, NLS0062, NLS0069, or NLS0089, respectively. In certain embodiments, the NLS0021, NLS0038, NLS0042, NLS0934, NLS0062, NLS0069, or NLS0089-related *Methylobacterium* is characterized by having a gene encoding a 16S RNA that has at least 95%, 97%, 98%, 99%, 99.5%, 99.7%, 99.9%, or 100% sequence identity across the entire length of SEQ ID NO: 1, 2, 3, 4, 5, 6, or 7, respectively. In certain embodiments of any of the aforementioned plant parts, the *Methylobacterium* is heterologous to the seed, tuber, or seedling. In certain embodiments of any of the aforementioned methods, the *Methylobacterium* is: (i) NLS0021 and the plant part is not a lettuce plant part; (ii) NLS0038 and the plant part is not a tomato plant part; (iii) NLS0042 or NLS0934 and the plant part is not a soybean plant part; (iv) NLS0062 or NLS0069 and the plant part is not a corn plant part; or (v) NLS0089 and the plant part is not a broccoli plant part. In certain embodiments of any of the aforementioned plant parts, the *Pratylenchus* sp. damage is selected from the group consisting of a reduction in plant growth, yield, water-deficit tolerance, chlorosis, produce quality, and combinations thereof. In certain embodiments of the aforementioned plant parts, the reduction in damage is evidenced by an increase in shoot weight, root weight, or the combination thereof in the plant in comparison to the control plant. In certain embodiments, such produce is a plant part. In certain embodiments of any of the aforementioned plant parts, the *Pratylenchus* sp. is selected from the group consisting of *Pratylenchus brachyurus, Pratylenchus coffeae, P. neglectus, Pratylenchus penetrans, Pratylenchus scribneri, Pratylenchus thornei, Pratylenchus vulnus*, and *Pratylenchus zeae*. In certain embodiments of any of the aforementioned plant parts, the plant part is selected from the group consisting of a *Brassica* sp. corn, wheat, rye, rice, alfalfa, rice, rye, sorghum, millet, soybean, tobacco, potato, peanut, carrot, cotton, coffee, coconut, pineapple, sugar beet, strawberry, oat, barley, tomato, lettuce, pepper, pea, onion, green bean, and cucurbit plant part.

Also provided are methods for controlling Root Lesion Nematode (RLN) damage to a plant that comprise: (i) applying a composition comprising at least one of an RLN-inhibitory *Methylobacterium* sp., a RLN-inhibitory cell-free culture supernatant, fraction thereof, concentrate thereof, and any combination thereof to soil where a plant is growing or will be grown. In certain embodiments, the composition comprises a solid substance with adherent RLN-active *Methylobacterium* grown thereon or an emulsion having RLN-inhibitory *Methylobacterium* grown therein; and, (ii) growing a plant or a plant from seed in soil subjected to the application of the composition and in the presence of RLN. Such methods may also be used for reducing the populations of RLN in soil. In certain embodiments of the methods, RLN damage sustained by the plant grown in the presence of the RLN is reduced in comparison to a control plant grown in the presence of the RLN. In certain embodiments of the methods, the composition comprises the RLN-inhibitory *Methylobacterium* sp. at a titer of about $5\times10^8$, $1\times10^9$, or $1\times10^{10}$ colony-forming units per gram of the solid substance to about $5\times10^{13}$ colony-forming units of *Methylobacterium* per gram of the solid substance or at a titer of about $1\times10^6$ CFU/mL to about $1\times10^9$ CFU/mL for the emulsion. In certain embodiments of the methods, the composition that is applied comprises the RLN-inhibitory *Methylobacterium* sp. at a titer of about $1\times10^4$ or $1\times10^5$ colony-forming units per ml to about $1\times10^9$, $1\times10^{10}$, $1\times10^{11}$, $5\times10^{11}$, or $1\times10^{12}$ colony-forming units of *Methylobacterium* per mL of a liquid or emulsion. In certain embodiments, about $1\times10^2$, $1\times10^3$, or $1\times10^4$ CFU to about $1\times10^8$ or $1\times10^9$ CFU of the RLN-inhibitory *Methylobacterium* sp. are provided on a 100 mm² surface of a plant part. In certain embodiments, about $1\times10^2$, $1\times10^3$, or $1\times10^4$ CFU to about $1\times10^8$ or $1\times10^9$ CFU of the RLN-inhibitory *Methylobacterium* sp. are provided on the surface of a seed. In certain embodiments of the methods, the RLN-inhibitory *Methylobacterium* sp. is a *Methylobacterium* isolate selected from the group consisting of *Methylobacterium* NLS0021, NLS0038, NLS0042, NLS0934, NLS0062, NLS0069, NLS0089, derivatives thereof, and *Methylobacterium* related thereto. In certain embodiments of any of the aforementioned methods, the composition is applied to the soil by broadcasting the composition, by drenching the soil with the composition, and/or by depositing the composition in furrow. In certain embodiments of the methods, the depositing in furrow is performed prior to placing seed in the furrow, at the same time as placing seed in the furrow, or after placing seed in the furrow. In certain embodiments of any of the aforementioned methods, the composition further comprises a nematicide that provides for inhibition of RLN growth, motility, and/or reproduction and/or reductions in RLN-mediated plant damage. In certain embodiments where the composition further comprises a nematicide, the nematicide is selected from the group consisting of an organophosphate, biological, and a carbamate nematicide. In certain embodiments of any of the aforementioned methods, soil in which the plant is to be grown is surveyed for the presence of RLN and the composition is applied to the soil when the RLN are present in the soil at a level that can result in reductions in plant growth, yield, water-deficit tolerance, chlorosis, produce quality, and combinations thereof to an untreated control plant. In certain embodiments of the methods, the composition is not applied to the soil when the RLN are present in the soil below levels that result in reductions in plant growth, yield, water-deficit tolerance, chlorosis, produce quality, and combinations thereof to an untreated control plant.

Methods for treating a plant seed that can provide a Root Lesion Nematodes (RLN) tolerant plant that comprises applying a composition comprising at least one of a RLN-inhibitory *Methylobacterium* sp., a RLN-inhibitory cell-free culture supernatant, fraction thereof, concentrates thereof, or any combination thereof to a seed, thereby obtaining a treated seed that can provide a RLN tolerant plant are also provided. In certain embodiments of the methods, RLN damage sustained by the RLN tolerant plant grown from the treated seed and in the presence of the RLN is reduced in comparison to RLN damage sustained by a control plant grown from an untreated seed in the presence of RLN. In certain embodiments of the methods, the composition comprises a solid substance with adherent RLN-inhibitory *Methylobacterium* grown thereon or an emulsion having RLN-inhibitory *Methylobacterium* grown therein. In certain embodiments of the methods, the composition comprises the RLN-inhibitory *Methylobacterium* sp. at a titer of about $5\times10^8$, $1\times10^9$, or $1\times10^{10}$ colony-forming units per gram of the solid substance to about $5\times10^{13}$ colony-forming units of *Methylobacterium* per gram of the solid substance or at a titer of about $1\times10^6$ CFU/mL to about $1\times10^9$ CFU/mL for the emulsion. In certain embodiments of the methods, the composition comprises the RLN-inhibitory *Methylobacterium* sp. at a titer of about $1\times10^4$ or $1\times10^5$ colony-forming units per ml to about $1\times10^9$, $1\times10^{10}$, $6\times10^{10}$, $1\times10^{11}$, $5\times10^{11}$, or $1\times10^{12}$ colony-forming units of *Methylobacterium* per mL of a liquid or emulsion. In certain embodiments, about $1\times10^2$, $1\times10^3$, or $1\times10^4$ CFU to about $1\times10^8$ or $1\times10^9$ CFU of the RLN-inhibitory *Methylobacterium* sp. are provided on the surface of the seed. In certain embodiments of the methods, the RLN-inhibitory *Methylobacterium* sp. is a *Methylobacterium* isolate selected from the group consisting of *Methylobacterium* NLS0021, NLS0038, NLS0042, NLS0934, NLS0062, NLS0069, NLS0089, derivatives thereof, and *Methylobacterium* related thereto. In certain embodiments of any of the aforementioned methods, the applied composition coats or partially coats the seed. Also provided herein are treated seeds obtained by any of the aforementioned methods. In certain embodiments of any of the aforementioned methods, the composition further comprises a nematicide that provides for inhibition of RLN growth, motility, and/or reproduction and/or reductions in RLN-mediated plant damage. In certain embodiments where the composition further comprises a nematicide, the nematicide is selected from the group consisting of an organophosphate, biological, and a carbamate nematicide.

Also provided herein are methods for controlling Root Lesion Nematodes (RLN) damage to a plant that comprise: (i) planting a seed that has been treated with a composition comprising at least one of a RLN-inhibitory *Methylobacterium* sp., a RLN-inhibitory cell-free culture supernatant, fraction thereof, concentrate thereof, or any combination thereof; and, (ii) growing a RLN-tolerant plant from the treated seed in the presence of RLN. In certain embodiments of the methods, the RLN damage sustained by the RLN-tolerant plant grown in the presence of the RLN is reduced in comparison to RLN damage sustained by a control plant grown from untreated seed in the presence of RLN. In certain embodiments of the methods, the seed was treated with a composition that comprises a solid substance with adherent RLN-inhibitory *Methylobacterium* grown thereon or an emulsion having RLN-inhibitory *Methylobacterium* grown therein. In certain embodiments of the methods, the composition comprises the RLN-inhibitory *Methylobacterium* sp. at a titer of about $5\times10^8$, $1\times10^9$, or $1\times10^{10}$ colony-forming units per gram of the solid substance to about $5\times10^{13}$ colony-forming units of *Methylobacterium* per gram of the solid substance or at a titer of about $1\times10^6$ CFU/mL to about $1\times10^9$ CFU/mL for the emulsion. In certain embodiments of the methods, the composition comprises the RLN-inhibitory *Methylobacterium* sp. at a titer of about $1\times10^4$ or $1\times10^5$ colony-forming units per ml to about $1\times10^9$, $1\times10^{10}$, $1\times10^{11}$, $5\times10^{11}$, or $1\times10^{12}$ colony-forming units of *Methylobacterium* per mL of a liquid or emulsion. In certain embodiments, about $1\times10^2$, $1\times10^3$, or $1\times10^4$ CFU to about $1\times10^8$ or $1\times10^9$ CFU of the RLN-inhibitory *Methylobacterium* sp. are provided on the surface of the seed. In certain embodiments of the methods, the RLN-inhibitory *Methylobacterium* sp. is a *Methylobacterium* isolate selected from the group consisting of *Methylobacterium* NLS0021, NLS0038, NLS0042, NLS0934, NLS0062, NLS0069, NLS0089, derivatives thereof, and *Methylobacterium* related thereto. In certain embodiments of any of the aforementioned methods, the applied composition coats or partially coats the seed. In certain embodiments of any of the aforementioned methods, the composition further comprises a nematicide that provides for inhibition of RLN growth, motility, and/or reproduction and/or reductions in RLN-mediated plant damage. In certain embodiments where the composition further comprises a nematicide, the nematicide is selected from the group consisting of a organophosphate, biological, and a carbamate nematicide.

Also provided are compositions comprising at least one of a RLN-inhibitory *Methylobacterium* sp., a RLN-inhibitory cell-free culture supernatant, fraction thereof, concentrate thereof, or any combination thereof and an agriculturally acceptable adjuvant and/or and agriculturally acceptable excipient. In certain embodiments, the composition comprises a solid substance with adherent RLN-inhibitory *Methylobacterium* grown thereon or an emulsion having RLN-inhibitory *Methylobacterium* grown therein. In certain embodiments, the composition comprises the RLN-inhibitory *Methylobacterium* sp. at a titer of about $5\times10^8$, $1\times10^9$, or $1\times10^{10}$ colony-forming units per gram of the solid substance to about $5\times10^{13}$ colony-forming units of *Methylobacterium* per gram of the solid substance or at a titer of about $1\times10^6$ CFU/mL to about $1\times10^9$ CFU/mL for the emulsion. In certain embodiments, the composition comprises the RLN-inhibitory *Methylobacterium* sp. at a titer of about $1\times10^4$ or $1\times10^5$ colony-forming units per ml to about $1\times10^9$, $1\times10^{10}$, or $6\times10^{10}$ colony-forming units of *Methylobacterium* per mL of a liquid or emulsion. In certain embodiments, about $1\times10^2$, $1\times10^3$, or $1\times10^4$ CFU to about $1\times10^8$ or $1\times10^9$ CFU of the RLN-inhibitory *Methylobacterium* sp. are provided on a 100 mm$^2$ surface of a plant part. In certain embodiments, about $1\times10^2$, $1\times10^3$, or $1\times10^4$ CFU to about $1\times10^8$ or $1\times10^9$ CFU of the RLN-inhibitory *Methylobacterium* sp. are provided on the surface of a seed. In certain embodiments, the RLN-inhibitory *Methylobacterium* sp. is selected from the group consisting of *Methylobacterium* NLS0021, NLS0038, NLS0042, NLS0934, NLS0062, NLS0069, NLS0089, derivatives thereof, and *Methylobacterium* related thereto. In certain embodiments, the composition further comprises a nematicide that provides for inhibition of RLN growth, motility, and/or reproduction and/or reductions in RLN-mediated plant damage. In certain embodiments, the nematicide is selected from the group consisting of an organophosphate, biological, and a carbamate nematicide. In any of the aforementioned compositions, the composition can be in a liquid form or in a dry form. In certain embodiments, the composition is in a dry, lyophilized form and further comprises a cryoprotectant. In certain embodiments, the compositions will be essentially free of contaminating microorganisms.

In certain embodiments of any of the aforementioned compositions comprising at least one of a RLN-inhibitory *Methylobacterium* sp., a RLN-inhibitory cell-free culture supernatant, fraction thereof, concentrate thereof, or any combination thereof, plants or plant part that is coated or partially coated with the composition, methods of using the compositions to control RLN damage to plants, plant parts, and plants derived therefrom, and methods of making the compositions, the RLN-inhibitory *Methylobacterium* sp. is heterologous to the plant or plant part to which it is applied.

In certain embodiments of any of the aforementioned compositions, plants, or plant part that is coated or partially coated with the compositions, methods of using the compositions to control RLN damage to plants, plant parts, and plants derived therefrom, methods of using the compositions to reduce populations of RLN in soil, and methods of making the compositions, the RLN-inhibitory *Methylobacterium* is selected from the group consisting of *Methylobacterium* NLS0021, NLS0038, NLS0042, NLS0934, NLS0062, NLS0069, NLS0089, and a derivative thereof.

Also provided are methods for obtaining a RLN-inhibitory cell-free culture supernatant comprising growing a *Methylobacterium* selected from the group consisting of NLS0021, NLS0038, NLS0042, NLS0934, NLS0062, NLS0069, NLS0089, derivatives thereof, and *Methylobacterium* related thereto in a culture comprising a liquid or an emulsion and separating the *Methylobacterium* from the culture supernatant, thereby obtaining a RLN-inhibitory cell-free culture supernatant. In certain embodiments, the methods further comprise the step of concentrating the cell-free culture supernatant. In certain embodiments, the methods further comprise the step of fractionating to cell-free supernatant. In certain embodiments, the methods further comprise the step of concentrating the cell-free supernatant. In certain embodiments of any of the aforementioned methods, the culture comprising a liquid or an emulsion further comprises a solid substance. Also provided are RLN-inhibitory cell-free culture supernatants, fractions thereof, or concentrates therefrom obtained by any of the aforementioned methods.

In certain embodiments of any of the aforementioned compositions, methods, plant, or plant parts, the RLN-inhibitory *Methylobacterium* sp. has a 16S RNA encoding sequence that has significant sequence identity to the 16S RNA encoding sequence of a RLN-inhibitory *Methylobacterium* sp. provided herein. In certain embodiments, the RLN-inhibitory *Methylobacterium* sp. has a 16S RNA encoding sequence that has at least 95%, 96%, 97%, 98%, 99%, or 99.5% sequence identity across the entire length of the 16S RNA encoding sequence of the RLN-inhibitory *Methylobacterium* sp. isolate NLS0021, NLS0038, NLS0042, NLS0934, NLS0062, NLS0069, or NLS0089 provided herein. A RLN active *Methylobacterium* sp. that can be used in any of the composition, plants or plant parts that are coated or partially coated with the compositions, methods of using the compositions to control RLN damage to plants, plant parts, and plants derived therefrom, and methods of making the compositions can be RLN active *Methylobacterium* sp. can be at least 95%, 96%, 97%, 98%, 99%, or 99.5% sequence identity across the entire length of the 16S RNA encoding sequences of SEQ ID NO: 1, 2, 3, 4, 5, 6, or 7.

In certain embodiments, methods for reducing the populations of Root Lesion Nematodes (RLN) in soil comprising: (a) applying a composition comprising a *Methylobacterium* selected from the group consisting of NLS0021, NLS0038, NLS0042, NLS0934, NLS0062, NLS0069, NLS0089, derivatives thereof, and *Methylobacterium* related thereto and an agriculturally acceptable excipient and/or an agriculturally acceptable adjuvant to a plant part to obtain a treated plant part; and (b) growing the plant from said treated plant part in the presence of RLN, wherein RLN populations are reduced in soil where the plant was grown in comparison to soil where a control plant from a control plant part that is not treated with the *Methylobacterium* was grown are provided. In certain embodiments, methods for reducing the populations of Root Lesion Nematodes (RLN) in soil comprising: (i) applying a composition comprising at least one of an RLN-inhibitory *Methylobacterium* sp., a RLN-inhibitory cell-free culture supernatant, fraction thereof, concentrate thereof, and any combination thereof to soil where a plant is growing or will be grown to obtain a treated soil; and (b) growing a plant in the treated soil and in the presence of RLN, wherein RLN populations are reduced in treated soil where the plant was grown in comparison to untreated soil where a control plant was grown are provided. In certain embodiments of the methods, the NLS0021, NLS0038, NLS0042, NLS0934, NLS0062, NLS0069, or NLS0089 derivative is obtained by mutagenizing or transforming *Methylobacterium* NLS0021, NLS0038, NLS0042, NLS0934, NLS0062, NLS0069, or NLS0089, respectively. In certain embodiments of the methods, the NLS0021, NLS0038, NLS0042, NLS0934, NLS0062, NLS0069, or NLS0089-related *Methylobacterium* is characterized by having a gene encoding a 16S RNA that has at least 95%, 96%, 97%, 98%, 99%, 99.5%, 99.7%, 99.9%, or 100% sequence identity across the entire length of SEQ ID NO: 1, 2, 3, 4, 5, 6, or 7, respectively. In certain embodiments of the methods, the *Methylobacterium* is heterologous to the plant or the plant part. In certain embodiments of the methods, the *Methylobacterium* is: (i) NLS0021 and the plant or plant part is not a lettuce plant or plant part; (ii) NLS0038 and the plant or plant part is not a tomato plant or plant part; (iii) NLS0042 or NLS0934 and the plant or plant part is not a soybean plant or plant part; (iv) NLS0062 or NLS0069 and the plant or plant part is not a corn plant or plant part; or (v) NLS0089 and the plant or plant part is not a broccoli plant or plant part. In certain embodiments of the methods, the plant or plant part is selected from the group consisting of a *Brassica* sp. corn, wheat, rye, rice, alfalfa, sorghum, millet, soybean, tobacco, potato, peanut, carrot, cotton, coffee, coconut, pineapple, sugar beet, strawberry, oat, barley, tomato, lettuce, pepper, pea, onion, green bean, and cucurbit plant or plant part. In certain embodiments of the aforementioned methods, the RLN populations are reduced in soil at least about 5%, at least about 10%, at least about 20%, at least about 30%, at least about 40%, at least about 50%, at least about 75%, at least about 85%, or at least about 95% in comparison to soil where a control plant from a control plant part that is not treated with the *Methylobacterium* was grown. In certain embodiments of the aforementioned methods, the RLN populations are reduced in the soil that had been treated by at least about 5%, at least about 10%, at least about 20%, at least about 30%, at least about 40%, at least about 50%, at least about 75%, at least about 85%, or at least about 95% in comparison to soil that had not been treated.

BRIEF DESCRIPTION OF THE DRAWINGS

Not Applicable.

DESCRIPTION

Definitions

As used herein, the phrases "adhered thereto" and "adherent" refer to *Methylobacterium* that are associated with a solid substance by growing, or having been grown, on a solid substance.

As used herein, the phrase "agriculturally acceptable adjuvant" refers to a substance that enhances the performance of an active agent in a composition for treatment of plants and/or plant parts. In certain compositions, an active agent can comprise a mono-culture or co-culture of *Methylobacterium*.

As used herein, the phrase "agriculturally acceptable excipient" refers to an essentially inert substance that can be used as a diluent and/or carrier for an active agent in a composition for treatment of plants and/or plant parts. In certain compositions, an active agent can comprise a mono-culture or co-culture of *Methylobacterium*.

As used herein, the term "*Methylobacterium*" refers to bacteria that are facultative methylotrophs of the genus *Methylobacterium*. The term *Methylobacterium*, as used herein, thus does not encompass species in the genera *Methylobacter*, *Methylomonas*, *Methylomicrobium*, *Methylococcus*, *Methylosinus*, *Methylocystis*, *Methylosphaera*, *Methylocaldum*, and *Methylocella*, which are obligate methanotrophs.

As used herein, the phrase "control plant" refers to a plant that had not received treatment with a RLN-inhibitory *Methylobacterium*, a RLN-inhibitory cell-free culture supernatant, fraction thereof, concentrate thereof, any combination thereof, or composition comprising the same at either the seed or any subsequent stage of the control plant's development. Control plants include, but are not limited to, un-treated plants, plants treated with compositions lacking any RLN-inhibitory agents, non-transgenic plants, transgenic plants having a transgene-conferred RLN resistance trait, and plants treated with, or grown in soil treated with, an insecticidal compound or other agent that can protect a plant from RLN feeding.

As used herein, the terms "Root Lesion Nematodes" and "RLN" are used interchangeable to refer to the juvenile or adult forms of any nematode of the genus *Pratylenchus*.

As used herein, the phrase "co-culture of *Methylobacterium*" refers to a *Methylobacterium* culture comprising at least two strains of *Methylobacterium* or at least two species of *Methylobacterium*.

As used herein, the phrase "contaminating microorganism" refers to microorganisms in a culture, fermentation broth, fermentation broth product, or composition that were not identified prior to introduction into the culture, fermentation broth, fermentation broth product, or composition.

As used herein, the phrase "derivatives thereof", when used in the context of a *Methylobacterium* isolate, refers to any strain that is obtained from the *Methylobacterium* isolate. Derivatives of a *Methylobacterium* isolate include, but are not limited to, variants of the strain obtained by selection, variants of the strain selected by mutagenesis and selection, and genetically transformed strains obtained from the *Methylobacterium* isolate.

As used herein, the term "emulsion" refers to a colloidal mixture of two immiscible liquids wherein one liquid is the continuous phase and the other liquid is the dispersed phase. In certain embodiments, the continuous phase is an aqueous liquid and the dispersed phase is liquid that is not miscible, or partially miscible, in the aqueous liquid.

As used herein, the phrase "essentially free of contaminating microorganisms" refers to a culture, fermentation broth, fermentation product, or composition where at least about 95% of the microorganisms present by amount or type in the culture, fermentation broth, fermentation product, or composition are the desired *Methylobacterium* or other desired microorganisms of pre-determined identity.

As used herein, the term "heterologous", when used in the context of *Methylobacterium*, cell-free culture supernatant, fraction thereof, or concentrate thereof that at least partially coats a plant or plant part, refers to a *Methylobacterium*, cell-free culture supernatant, fraction thereof, or concentrate thereof that is not naturally associated with a plant or plant part of the same species as the plant or plant part that is at least partially coated with the *Methylobacterium*, cell-free culture supernatant, fraction thereof, or concentrate thereof. In certain embodiments, the heterologous *Methylobacterium* that is used to at least partially coat a plant or plant part of a first plant species is a *Methylobacterium* that was isolated, or can be isolated, from a second and distinct plant species. In certain embodiments, the heterologous *Methylobacterium* cell-free culture supernatant, fraction thereof, or concentrate thereof that is used to at least partially coat a plant or plant part of a first plant species is obtained from a *Methylobacterium* that was isolated, or can be isolated, from a second and distinct plant species.

As used herein, the phrase "inanimate solid substance" refers to a substance which is insoluble or partially soluble in water or aqueous solutions and which is either non-living or which is not a part of a still-living organism from which it was derived.

As used herein, the phrase "mono-culture of *Methylobacterium*" refers to a *Methylobacterium* culture consisting of a single strain of *Methylobacterium*.

As used herein, the phrase "partially coated", when used in the context of a composition comprising a RLN-inhibitory *Methylobacterium* sp. and a plant part (e.g., a seed), refers to a plant part where at least 10%, 20%, 40%, 50%, 60%, 70%, 80%, 90%, or 95% of the surface area of the plant part is coated with the composition.

As used herein, the term "peptide" refers to any polypeptide of 50 amino acid residues or less.

As used herein, the term "protein" refers to any polypeptide having 51 or more amino acid residues.

As used herein, a "pesticide" refers to an agent that is insecticidal, fungicidal, nematocidal, bacteriocidal, or any combination thereof.

As used herein, the phrase "bacteriostatic agent" refers to agents that inhibit growth of bacteria but do not kill the bacteria.

As used herein, the phrase "pesticide does not substantially inhibit growth of said *Methylobacterium*" refers to any pesticide that when provided in a composition comprising a fermentation product comprising a solid substance wherein a mono-culture or co-culture of *Methylobacterium* is adhered thereto, results in no more than a 50% inhibition of *Methylobacterium* growth when the composition is applied to a plant or plant part in comparison to a composition lacking the pesticide. In certain embodiments, the pesticide results in no more than a 40%, 20%, 10%, 5%, or 1% inhibition of *Methylobacterium* growth when the composition is applied to a plant or plant part in comparison to a composition lacking the pesticide.

As used herein, the term "PPFM. bacteria" refers without limitation to bacterial species in the genus *Methylobacterium* other than *M. nodulans*.

As used herein, the phrase "solid substance" refers to a substance which is insoluble or partially soluble in water or aqueous solutions.

As used herein, the phrase "solid phase that can be suspended therein" refers to a solid substance that can be distributed throughout a liquid by agitation.

As used herein, the term "non-regenerable" refers to either a plant part or processed plant product that cannot be regenerated into a whole plant.

To the extent to which any of the preceding definitions is inconsistent with definitions provided in any patent or non-patent reference incorporated herein by reference, any patent or non-patent reference cited herein, or in any patent or non-patent reference found elsewhere, it is understood that the preceding definition will be used herein.

RLN-Inhibitory *Methylobacterium*, Compositions Comprising RLN-Inhibitory *Methylobacterium* and/or RLN-Inhibitory Cell Free Culture Supernatants, Fractions, or Concentrates Thereof, Methods of their Use, and Methods of Making Various RLN-inhibitory *Methylobacterium* isolates, compositions comprising these *Methylobacterium*, and/or RLN-inhibitory cell free culture supernatants, fractions, or concentrates thereof, methods of using the compositions to inhibit RLN growth, motility, or reproduction and/or reduce RLN damage to a plant, and methods of making the compositions are provided herein. As used herein, inhibition of the growth, motility, or reproduction of a RLN includes any measurable decrease in RLN growth, motility, and/or reproduction, where RLN growth, motility, and/or reproduction includes, but is not limited to, any measurable increase in the juvenile weight, any measurable movement, and/or any progression through juvenile development stages or from juvenile to adult development. As used herein, inhibition of RLN growth, motility, and/or reproduction and/or reduction of RLN damage to a plant are also understood to include any measurable decrease in RLN infection and/or the adverse effects or damage caused by RLN feeding on a plant. Adverse effects of RLN infection on a plant include, but are not limited to, deformation and/or reductions in root systems, reductions in top growth, any type of tissue damage or necrosis, increased incidence of fungal or bacterial disease, any type of yield reduction, and/or decreased water-deficit tolerance.

Isolated RLN-inhibitory *Methylobacterium* sp. are provided herein. In certain embodiments, the RLN-inhibitory *Methylobacterium* isolate is selected from the group consisting of *Methylobacterium* NLS0021, NLS0038, NLS0042, NLS0934, NLS0062, NLS0069, NLS0089, derivatives thereof, and *Methylobacterium* related thereto. In certain embodiments, the RLN-inhibitory *Methylobacterium* isolate is selected from the group consisting of *Methylobacterium* NLS0021, NLS0038, NLS0069, and a derivative thereof. In certain embodiments, the RLN-inhibitory *Methylobacterium* provides for at least about 25%, at least about 50%, or at least about 75% reductions in RLN damage to a treated plant, plant arising from a treated seed, or plant grown in soil treated with the RLN in comparison to untreated control plants, plants arising from untreated seeds, or plants grown in untreated soils upon exposure to a RLN. In certain embodiments, the RLN-inhibitory *Methylobacterium* provides for increased yield, shoot weight, or root weight in the treated plant, plant part, or a plant derived therefrom relative to an untreated control plant, plant part, or a plant derived therefrom. In certain embodiments, a cell-free culture supernatant or active ingredient contained therein from an RLN-inhibitory *Methylobacterium* provides for decreased motility or viability of RLN obtained from the treated plant, plant part, or a plant derived therefrom relative to an untreated control plant, plant part, or a plant derived therefrom. In certain embodiments, the RLN-inhibitory *Methylobacterium*, a cell-free culture supernatant obtained therefrom, or an active ingredient contained in the cell-free culture supernatant provides for increased yield, shoot weight, or root weight in the treated plant, plant part, or a plant derived therefrom relative to an untreated control plant, plant part, or a plant derived therefrom. In certain embodiments, the RLN that is inhibited is selected from the group consisting of a *Pratylenchus brachyurus, Pratylenchus coffeae, P. neglectus, Pratylenchus penetrans, Pratylenchus scribneri, Pratylenchus thornei, Pratylenchus vulnus*, and *Pratylenchus zeae.*

In certain embodiments, the RLN-inhibitory *Methylobacterium*, a cell-free culture supernatant obtained therefrom, fraction thereof, concentrate thereof, or an active ingredient contained in the cell-free culture supernatant provides for at least about 25%, at least about 50%, or at least about 75% reductions in RLN motility, viability, growth, and/or reproduction on a treated plant, plant arising from a treated seed, or plant grown in soil treated with the RLN-inhibitory *Methylobacterium* in comparison to a untreated control plants, plants arising from untreated seeds, or plants grown in untreated soils upon exposure to a RLN. In certain embodiments, the RLN-inhibitory *Methylobacterium* is a *Methylobacterium* that inhibits a *Pratylenchus* sp. is selected from the group consisting of a *Pratylenchus brachyurus*, *Pratylenchus coffeae*, *P. neglectus*, *Pratylenchus penetrans*, *Pratylenchus scribneri*, *Pratylenchus thornei*, *Pratylenchus vulnus*, and *Pratylenchus zeae* species. In certain embodiments of any of the aforementioned compositions, the composition comprises a solid substance wherein a mono-culture or co-culture of *Methylobacterium* is adhered thereto. In certain embodiments where the *Methylobacterium* is adhered to a solid substance, the composition comprises a colloid formed by the solid substance wherein a mono-culture or co-culture of *Methylobacterium* is adhered thereto and a liquid. In certain embodiments, the colloid is a gel. In certain embodiments of certain aforementioned compositions, composition is an emulsion that does not contain a solid substance. In certain embodiments of any of the aforementioned compositions, the RLN-inhibitory *Methylobacterium* is selected from the group consisting of *Methylobacterium* NLS0021, NLS0038, NLS0042, NLS0934, NLS0062, NLS0069, NLS0089, derivatives thereof, and *Methylobacterium* related thereto. In certain embodiments of any of the aforementioned compositions, the RLN-inhibitory *Methylobacterium* is selected from the group consisting of *Methylobacterium* NLS0021, NLS0038, NLS0069, and a derivative thereof.

In certain embodiments, isolated RLN-inhibitory *Methylobacterium* sp., a cell-free culture supernatant obtained therefrom, fraction thereof, or concentrate thereof can be identified by treating a plant, a seed, soil in which the plant or a plant arising from the seed are grown, or other plant growth media in which the plant or a plant arising from the seed are grown and assaying for either reductions in RLN damage, RLN growth, RLN reproduction, RLN feeding activity, RLN motility, numbers of recovered RLN, and combinations thereof. In still other embodiments, the RLN-inhibitory *Methylobacterium* sp., compositions comprising the same, fermentation products comprising the same, cell free culture supernatants therefrom, fractions therefrom, concentrates therefrom, or compounds derived therefrom can be exposed to juvenile RLN and assayed for inhibition of juvenile growth, development, behavior, motility, or feeding activity. Various assays for determining quantity and/or activity of RLN that can be adapted for use in identifying RLN-inhibitory cell-free culture supernatants, fractions therefrom, or concentrates thereof, and RLN-inhibitory *Methylobacterium* sp. have been disclosed (Hollaway et al. Australasian Plant Pathology, 2003, 32(1):73-79; Kimura et al. Agric. Biol. Chem., 1981, 45 (1), 249-251).

In certain embodiments, the RLN-inhibitory *Methylobacterium* sp. has a 16S RNA encoding sequence that has significant sequence identity to the 16S RNA encoding sequence of a RLN-inhibitory *Methylobacterium* sp. provided herein. In certain embodiments, the RLN-inhibitory *Methylobacterium* sp. has a 16S RNA encoding sequence that has at least 95%, 96%, 97%, 98%, 99%, or 99.5% sequence identity across the entire length of the 16S RNA encoding sequence of an RLN-inhibitory *Methylobacterium* sp. isolate NLS0021, NLS0038, NLS0042, NLS0934, NLS0062, NLS0069, or NLS0089. A RLN-inhibitory *Methylobacterium* sp. that can be used in any of the composition, plants or plant parts that are coated or partially coated with the compositions, methods of using the compositions to control RLN damage to plants, plant parts, and plants derived therefrom, and methods of making the compositions can be RLN-inhibitory *Methylobacterium* sp. can be at least 95%, 96%, 97%, 98%, 99%, or 99.5% sequence identity across the entire length of the 16S RNA encoding sequences of SEQ ID NO: 1, 2, 3, 4, 5, 6, or 7. The 16S RNA encoding sequence of SEQ ID NO: 1-7 are set forth in Table 1.

TABLE 1

| 16S RNA encoding sequences | | |
|---|---|---|
| Isolate (NLS No.) | SEQ ID NO: | DNA sequence encoding the 16S RNA |
| NLS0021 | SEQ ID NO: 1 | GAGTTTGATCCTGGCTCAGAGCGAACGCT GGCGGCAGGCTTAACACATGCAAGTCGA ACGGGCTTCTTCGGAAGTCAGTGGCAGAC GGGTGAGTAACACGTGGGAACGTGCCCTT CGGTTCGGAATAACTCAGGGAAACTTGA GCTAATACCGGATACGCCCTTATGGGGAA AGGTTTACTGCCGAAGGATCGGCCCGCGT CTGATTAGCTTGTTGGTGGGGTAACGGCC TACCAAGGCGACGATCAGTAGCTGGTCTG AGAGGATGATCAGCCACACTGGGACTGA GACACGGCCCAGACTCCTACGGGAGGCA GCAGTGGGGAATATTGGACAATGGGCGC AAGCCTGATCCAGCCATGCCGCGTGAGTG ATGAAGGCCTTAGGGTTGTAAAGCTCTTT TGTCCGGGACGATAATGACGGTACCGGA AGAATAAGCCCCGGCTAACTTCGTGCCAG CAGCCGCGGTAATACGAAGGGGGCTAGC GTTGCTCGGAATCACTGGGCGTAAAGGGC GCGTAGGCGGCCGATTAAGTCGGGGGTG AAAGCCTGTGGCTCAACCACAGAATTGCC TTCGATACTGGTTGGCTTGAGACCGGAAG AGGACAGCGGAACTGCGAGTGTAGAGGT GAAATTCGTAGATATTCGCAAGAACACCA GTGGCGAAGGCGGCTGTCTGGTCCGGTTC TGACGCTGAGGCGCGAAAGCGTGGGGAG CAAACAGGATTAGATACCCTGGTAGTCCA CGCCGTAAACGATGAATGCCAGCCGTTGG TCTGCTTGCAGGTCAGTGGCGCCGCTAAC GCATTAAGCATTCCGCCTGGGGAGTACGG TCGCAAGATTAAAACTCAAAGGAATTGA CGGGGGCCCGCACAAGCGGTGGAGCATG TGGTTTAATTCGAAGCAACGCGCAGAACC TTACCATCCCTTGACATGGCATGTTACCT CGAGAGATCGGGGATCCTCTTCGGAGGC GTGCACACAGGTGCTGCATGGCTGTCGTC AGCTCGTGTCGTGAGATGTTGGGTTAAGT CCCGCAACGAGCGCAACCCACGTCCTTAG TTGCCATCATTCAGTTGGGCACTCTAGGG AGACTGCCGGTGATAAGCCGCGAGGAAG GTGTGGATGACGTCAAGTCCTCATGGCCC TTACGGGATGGGCTACACACGTGCTACAA TGGCGGTGACAGTGGGACGCGAAACCGC GAGGTTGAGCAAATCCCCAAAAGCCGTCT CAGTTCGGATTGCACTCTGCAACTCGGGT GCATGAAGGCGGAATCGCTAGTAATCGT GGATCAGCACGCCACGGTGAATACGTTCC CGGGCCTTGTACACACCGCCCGTCACACC ATGGGAGTTGGTCTTACCCGACGGCGCTG CGCCAACCGCAAGGGGGCAGGCGACCAC GGTAGGGTCAGCGACTGGGGTGAAGTCG TAACAAGGTAGCCGTAGGGGAACCTGCG GCTGGATCACCT |
| NLS0038 | SEQ ID NO: 2 | GGTGATCCAGCCGCAGGTTCCCCTACGGC TACCTTGTTACGACTTCACCCCAGTCGCT GACCCTACCGTGGTCGCCTGCCTCCTTGC GGTTGGCGCAGCGCCGTCGGGTAAGACC AACTCCCATGGTGTGACGGGCGGTGTGTA CAAGGCCCGGGAACGTATTCACCGTGGC |

TABLE 1-continued

16S RNA encoding sequences

| Isolate (NLS No.) | SEQ ID NO: | DNA sequence encoding the 16S RNA |
|---|---|---|
| | | GTGCTGATCCACGATTACTAGCGATTCCG
CCTTCATGCACCCGAGTTGCAGAGTGCAA
TCCGAACTGAGACGGTTTTTGGGGATTTG
CTCCACCTCGCGGCTTCGCGTCCCACTGT
CACCGCCATTGTAGCACGTGTGTAGCCCA
TCCCGTAAGGGCCATGAGGACTTGACGTC
ATCCACACCTTCCTCGCGGCTTATCACCG
GCAGTCTCCCTAGAGTGCCCAACTGAATG
ATGGCAACTAAGGACGTGGGTTGCGCTCG
TTGCGGGACTTAACCCAACATCTCACGAC
ACGAGCTGACGACAGCCATGCAGCACCT
GTGTGCACGCCTCCGAAGAGGATCCCCGA
TCTCTCGAGGTAACATGCCATGTCAAGGG
ATGGTAAGGTTCTGCGCGTTGCTTCGAAT
TAAACCACATGCTCCACCGCTTGTGCGGG
CCCCCGTCAATTCCTTTGAGTTTTAATCTT
GCGACCGTACTCCCCAGGCGGAATGCTTA
ATGCGTTAGCGGCGCCACTGACCTGCAAG
CAGGCCAACGGCTGGCATTCATCGTTTAC
GGCGTGGACTACCAGGGTATCTAATCCTG
TTTGCTCCCCACGCTTTCGCGCCTCAGCGT
CAGAACCGGACCAGACAGCCGCCTTCGC
CACTGGTGTTCTTGCGAATATCTACGAAT
TTCACCTCTACACTCGCAGTTCCGCTGTCC
TCTTCCGGTCTCAAGCCAACCAGTATCGA
AGGCAATTCTGTGGTTGAGCCACAGGCTT
TCACCCCCGACTTAATCGGCCGCCTACGC
GCCCTTTACGCCCAGTCAGTCGGATTCCGAGCAAC
GCTAGCCCCCTTCGTATTACCGCGGCTGC
TGGCACGAAGTTAGCCGGGGCTTATTCTT
CCGGTACCGTCATTATCGTCCCGGACAAA
AGAGCTTTACAACCCTAAGGCCTTCATCA
CTCACGCGGCATGGCTGGATCAGGCTTGC
GCCCATTGTCCAATATTCCCCACTGCTGC
CTCCCGTAGGAGTCTGGGCCGTGTCTCAG
TCCCAGTGTGGCTGATCATCCTCTCAGAC
CAGCTACTGATCGTCGCCTTGGTAGGCCG
TTACCCCACCAACAAGCTAATCAGACGCG
GGCCGATCCTTCGGCAGTAAACCTTTCCC
CAAAAGGGCGTATCCGGTATTAGCTCAAG
TTTCCCTGAGTTATTCCGAACCGAAGGGT
ACGTTCCCACGTGTTACTCACCCGTCTGC
CACTGACACCCGAAGGTGCCCGTTCGACT
TGCATGTGTTAAGCCTGCCGCCAGCGTTC
GCTCTGAGCCAGGATCAAACTCT |
| NLS0042 | SEQ ID NO: 3 | GAGTTTGATCCTGGCTCAGAGCGAACGCT
GGCGGCAGGCTTAACACATGCAAGTCGA
ACGGGCACCTTCGGGTGTCAGTGGCAGAC
GGGTGAGTAACACGTGGGAACGTACCCTT
CGGTTCGGAATAACTCAGGGAAACTTGA
GCTAATACCGGATACGCCCTTTTGGGGAA
AGGTTTACTGCCGAAGGATCGGCCCGCGT
CTGATTAGCTTGTTGGTGGGGTAACGGCC
TACCAAGGCGACGATCAGTAGCTGGTCTG
AGAGGATGATCAGCCACACTGGGACTGA
GACACGGCCCAGACTCCTACGGGAGGCA
GCAGTGGGGAATATTGGACAATGGGCGC
AAGCCTGATCCAGCCATGCCGCGTGAGTG
ATGAAGGCCTTAGGGTTGTAAAGCTCTTT
TGTCCGGACGATAATGACGGTACCGGA
AGAATAAGCCCCGGCTAACTTCGTGCCAG
CAGCCGCGGTAATACGAAGGGGGCTAGC
GTTGCTCGGAATCACTGGGCGTAAAGGGC
GCGTAGGCGGCCGATTAAGTCGGGGGTG
AAAGCCTGTGCTCAACCACAGAATTGCC
TTCGATACTGGTTGGCTTGAGACCGGAAG
AGGACAGCGGAACTGCGAGTGTAGAGGT
GAAATTCGTAGATATTCGCAAGAACACCA
GTGGCGAAGGCGGTCGTCTGGTCCGGTTC
TGACGCTGAGGCGCGAAAGCGTGGGGAG
CAAACAGGATTAGATACCCTGGTAGTCCA
CGCCGTAAACGATGAATGCCAGCCGTTGG
CCTGCTTGCAGGTCAGTGGCGCCGCTAAC
GCATTAAGCATTCCGCCTGGGGAGTACGG |

TABLE 1-continued

16S RNA encoding sequences

| Isolate (NLS No.) | SEQ ID NO: | DNA sequence encoding the 16S RNA |
|---|---|---|
| | | TCGCAAGATTAAAACTCAAAGGAATTGA
CGGGGGCCCGCACAAGCGGTGGAGCATG
TGGTTTAATTCGAAGCAACGCGCAGAACC
TTACCATCCCTTGACATGGCATGTTACCT
CGAGAGATCGGGGATCCTCTTCGGAGGC
GTGCACACAGGTGCTGCATGGCTGTCGTC
AGCTCGTGTCGTGAGATGTTGGGTTAAGT
CCCGCAACGAGCGCAACCCACGTCCTTAG
TTGCCATCATTCAGTTGGGCACTCTAGGG
AGACTGCCGGTGATAAGCCGCGAGGAAG
GTGTGGATGACGTCAAGTCCTCATGGCCC
TTACGGGATGGGCTACACACGTGCTACAA
TGGCGGTGACAGTGGGACGCGAAGCCGC
GAGGTGGAGCAAATCCCCAAAAACCGTC
TCAGTTCGGATTGCACTCTGCAACTCGGG
TGCATGAAGGCGGAATCGCTAGTAATCGT
GGATCAGCACGCCACGGTGAATACGTTCC
CGGGCCTTGTACACACCGCCCGTCACACC
ATGGGAGTTGGTCTTACCCGACGGCGCTG
CGCCAACCGCAAGGAGGCAGGCGACCAC
GGTAGGGTCAGCGACTGGGGTGAAGTCG
TAACAAGGTAGCCGTAGGGGAACCTGCG
GCTGGATCACCT |
| NLS0934 | SEQ ID NO: 4 | GAGTTTGATCCTGGCTCAGAGCGAACGCT
GGCGGCAGGCTTAACACATGCAAGTCGA
ACGCACCGCAAGGTGAGTGGCAGACGGG
TGAGTAACACGTGGGAACGTGCCCTCCGG
TCTGGGATAACCCTGGGAAACTAGGGCTA
ATACCGGATACGTGCTTTGGCAGAAAGGT
TTACTGCCGGAGGATCGGCCCGCGTCTGA
TTAGCTTGTTGGTGGGGTAACGGCCTACC
AAGGCGACGATCAGTAGCTGGTCTGAGA
GGATGATCAGCCACACTGGGACTGAGAC
ACGGCCCAGACTCCTACGGGAGGCAGCA
GTGGGGAATATTGGACAATGGGCGCAAG
CCTGATCCAGCCATGCCGCGTGAGTGATG
ACGGCCTTAGGGTTGTAAAGCTCTTTTCT
CCGGGACGATAATGACGGTACCGGAGGA
ATAAGCCCCGGCTAACTTCGTGCCAGCAG
CCGCGGTAATACGAAGGGGGCTAGCGTT
GCTCGGAATCACTGGGCGTAAAGGGCGC
GTAGGCGGCGTTTAAGTCGGGGGTGAA
AGCCTGTGGCTCAACCACAGAATGGCCTT
CGATACTGGGACGCTTGAGTATGGTAGAG
GTTGGTGGAACTGCGAGTGTAGAGGTGA
AATTCGTAGATATTCGCAAGAACACCGGT
GGCGAAGGCGGCCAACTGGACCATTACT
GACGCTGAGGCGAAAGCGTGGGGAGC
AAACAGGATTAGATACCCTGGTAGTCCAC
GCCGTAAACGATGAATGCTAGCTGTTGGG
GTGCATGCACCGCAGTAGCGCAGCTAAC
GCATTAAGCATTCCGCCTGGGGAGTACGG
TCGCAAGATTAAAACTCAAAGGAATTGA
CGGGGGCCCGCACAAGCGGTGGAGCATG
TGGTTTAATTCGAAGCAACGCGCAGAACC
TTACCATCCTTTGACATGGCGTGTTACTG
GGAGAGATTCCAGGTCCCCTTCGGGGGCG
CGCACACAGGTGCTGCATGGCTGTCGTCA
GCTCGTGTCGTGAGATGTTGGGTTAAGTC
CCGCAACGAGCGCAACCCACGTCCTTAGT
TGCCATCATTTGGTTGGGCACTCTAGGGA
GACTGCCGGTGATAAGCCGCGAGGAAGG
TGTGGATGACGTCAAGTCCTCATGGCCCT
TACGGGATGGGCTACACACGTGCTACAAT
GGCGGTGACAGTGGGACGCGAAGGGTG
ACCCGGAGCCAATCTCCAAAAGCCGTCTC
AGTTCGGATTGCACGCTGCAACTCGCGTG
CATGAAGGCGGAATCGCTAGTAATCGTG
GATCAGCATGCCACGGTGAATACGTTCCC
GGGCCTTGTACACACCGCCCGTCACACCA
TGGGAGTTGGTCTTACCCGACGGCGCTGC
GCCAACCAAATCGAGCTTGCTCGACTGGA
GGCAGGCGACCACGGTAGGGTCAGCGAC |

TABLE 1-continued

16S RNA encoding sequences

| Isolate (NLS No.) | SEQ ID NO: | DNA sequence encoding the 16S RNA |
|---|---|---|
| | | TGGGGTGAAGTCGTAACAAGGTAGCCGT AGGGGAACCTGCGGCTGGATCACCT |
| NLS0062 | SEQ ID NO: 5 | GGTGATCCAGCCGCAGGTTCCCCTACGGC TACCTTGTTACGACTTCACCCCAGTCGCT GACCCTACCGTGGTCGCCTGCCTCCTTGC GGTTGGCGCAGCGCCGTCGGGTAAGACC AACTCCCATGGTGTGACGGGCGGTGTGTA CAAGGCCCGGGAACGTATTCACCGTGGC GTGCTGATCCACGATTACTAGCGATTCCG CCTTCATGCACCCGAGTTGCAGAGTGCAA TCCGAACTGAGACGGCTTTTGGGGATTTG CTCCACCTCGCGGCTTCGCGTCCCACTGT CACCGCCATTGTAGCACGTGTGTAGCCCA TCCCGTAAGGGCCATGAGGACTTGACGTC ATCCACACCTTCCTCGCGGCTTATCACCG GCAGTCTCCCTAGAGTGCCCAACTGAATG ATGGCAACTAAGGACGTGGGTTGCGCTCG TTGCGGGACTTAACCCAACATCTCACGAC ACGAGCTGACGACAGCCATGCAGCACCT GTGTGCACGCCTCCGAAGAGGATCCCCGA TCTCTCGAGGTAACATGCCATGTCAAGGG ATGGTAAGGTTCTGCGCGTTGCTTCGAAT TAAACCACATGCTCCACCGCTTGTGCGGG CCCCCGTCAATTCCTTTGAGTTTTAATCTT GCGACCGTACTCCCCAGGCGGAATGCTTA ATGCGTTAGCGGCGCCACTGACCTGCAAG CAGGCCAACGGCTGGCATTCATCGTTTAC GGCGTGGACTACCAGGGTATCTAATCCTG TTTGCTCCCCACGCTTTCGCGCCTCAGCGT CAGAACCGGACCAGACAGCCGCCTTCGC CACTGGTGTTCTTGCGAATATCTACGAAT TTCACCTCTACACTCGCAGTTCCGCTGTCC TCTTCCGGTCTCAAGCCAACCAGTATCGA AGGCAATTCTGTGGTTGAGCCACAGGCTT TCACCCCCGACTTAATCGGCCGCCTACGC GCCCTTTACGCCCAGTGATTCCGAGCAAC GCTAGCCCCCTTCGTATTACCGCGGCTGC TGGCACGAAGTTAGCCGGGGCTTATTCTT CCGGTACCGTCATTATCGTCCCGGACAAA AGAGCTTTACAACCCTAAGGCCTTCATCA CTCACGCGGCATGGCTGGATCAGGCTTGC GCCCATTGTCCAATATTCCCCACTGCTGC CTCCCGTAGGAGTCTGGGCCGTGTCTCAG TCCCAGTGTGGCTGATCATCCTCTCTCAGAC CAGCTACTGATCGTCGCCTTGGTAGGCCG TTACCCCACCAACAAGCTAATCAGACGCG GGCCGATCCTTCGGCAGTAAACCTTTCCC CAAAAGGGCGTATCCGGTATTAGCTCAAG TTTCCCTGAGTTATTCCGAACCGAAGGGT ACGTTCCCACGTGTTACTCACCCGTCTGC CACTGACACCCGAAGGTGCCCGTTCGACT TGCATGTGTTAAGCCTGCCGCCAGCGTTC GCTCTGAGCCAGGATCAAACTCT |
| NLS0069 | SEQ ID NO: 6 | GGTGATCCAGCCGCAGGTTCCCCTACGGC TACCTTGTTACGACTTCACCCCAGTCGCT GACCCTACCGTGGTCGCCTGCCTCCTTGC GGTTGGCGCAGCGCCGTCGGGTAAGACC AACTCCCATGGTGTGACGGGCGGTGTGTA CAAGGCCCGGGAACGTATTCACCGTGGC ATGCTGATCCACGATTACTAGCGATTCCG CCTTCATGCACCCGAGTTGCAGAGTGCAA TCCGAACTGAGACGGCTTTTGGGGATTTG CTCAACCTCGCGGTTTCGCGTCCCACTGT CACCGCCATTGTAGCACGTGTGTAGCCCA TCCCGTAAGGGCCATGAGGACTTGACGTC ATCCACACCTTCCTCGCGGCTTATCACCG GCAGTCTCCCTAGAGTGCCCAACTGAATG ATGGCAACTAAGGACGTGGGTTGCGCTCG TTGCGGGACTTAACCCAACATCTCACGAC ACGAGCTGACGACAGCCATGCAGCACCT GTGTGCAGGTCCCCGAAGGGAACGACCG ATCTCTCGGACAATCCTGCCATGTCAAGG GATGGTAAGGTTCTGCGCGTTGCTTCGAA |
| | | TTAAACCACATGCTCCACCGCTTGTGCGG GCCCCCGTCAATTCCTTTGAGTTTTAATCT TGCGACCGTACTCCCCAGGCGGAATGCTT AATGCGTTAGCGGCGCCACTGACCTGCAA GCAGACCAACGGCTGGCATTCATCGTTTA CGGCGTGGACTACCAGGGTATCTAATCCT GTTTGCTCCCCACGCTTTCGCGCCTCAGC GTCAGAACCGGACCAGACAGCCGCCTTC GCCACTGGTGTTCTTGCGAATATCTACGA ATTTCACCTCTACACTCGCAGTTCCGCTGT CCTCTTCCGGTCTCAAGCTTTCCAGTATCG AAGGCAATTCTGTGGTTGAGCCACAGGCT TTCACCCCCGACTTAAAAAGCCGCCTACG CGCCCTTTACGCCCAGTGATTCCGAGCAA CGCTAGCCCCCTTCGTATTACCGCGGCTG CTGGCACGAAGTTAGCCGGGGCTTATTCT TCCGGTACCGTCATTATCGTCCCGGACAA AAGAGCTTTACAACCCTAAGGCCTTCATC ACTCACGCGGCATGGCTGGATCAGGCTTG CGCCCATTGTCCAATATTCCCCACTGCTG CCTCCCGTAGGAGTCTGGGCCGTGTCTCA GTCCCAGTGTGGCTGATCATCCTCTCAGA CCAGCTACTGATCGTCGCCTTGGTAGGCC GTTACCCCACCAACTAGCTAATCAGACGC GGGCCGATCCTTCGGCAGTAAACCTTTCC CCAAAAGGGCGTATCCGGTATTAGCTCAA GTTTCCCTGAGTTATTCCGAACCGAAGGG CACGTTCCCACGTGTTACTCACCCGTCTG CCGCTGACCCCGAAGGGCCCGCTCGACTT GCATGTGTTAAGCCTGCCGCCAGCGTTCG CTCTGAGCCAGGATCAAACTCT |
| NLS0089 | SEQ ID NO: 7 | GAGTTTGATCCTGGCTCAGAGCGAACGCT GGCGGCAGGCTTAACACATGCAAGTCGA ACGGGCTTCTTCGGAAGTCAGTGGCAGAC GGGTGAGTAACACGTGGGAACGTGCCCTT CGGTTCGGAATAACTCAGGGAAACTTGA GCTAATACCGGATACGCCCTTACGGGGAA AGGTTTACTGCCGAAGGATCGGCCCGCGT CTGATTAGCTTGTTGGTGGGTAACGGCCC TACCAAGGCGACGATCAGTAGCTGGTCTG AGAGGATGATCAGCCACACTGGGACTGA GACACGGCCCAGACTCCTACGGGAGGCA GCAGTGGGAATATTGGACAATGGGCGC AAGCCTGATCCAGCCATGCCGCGTGAGTG ATGAAGGCCTTAGGGTTGTAAAGCTCTTT TGTCCGGGACGATAATGACGGTACCGGA AGAATAAGCCCCGGCTAACTTCGTGCCAG CAGCCGCGGTAATACGAAGGGGGCTAGC GTTGCTCGGAATCACTGGGCGTAAAGGGC GCGTAGGCGGCCGATTAAGTCGGGGGTG AAAGCCTGTGGCTCAACCACAGAATTGCC TTCGATACTGGTTGGCTTGAGACCGGAAG AGGACAGCGGAACTGCGAGTGTAGAGGT GAAATTCGTAGATATTCGCAAGAACACCA GTGGCGAAGGCGGCTGTCTGGTCCGGTTC TGACGCTGAGGCGCGAAAGCGTGGGGAG CAAACAGGATTAGATACCCTGGTAGTCCA CGCCGTAAACGATGAATGCCAGCCGTTGG TCTGCTTGCAGGTCAGTGGCGCCGCTAAC GCATTAAGCATTCCGCCTGGGGAGTACGG TCGCAAGATTAAAACTCAAAGGAATTGA CGGGGGCCCGCACAAGCGGTGGAGCATG TGGTTTAATTCGAAGCAACGCGCAGAACC TTACCATCCCTTGACATGGCATGTTACCT CGAGAGATCGGGATCCTCTTCGGAGGC GTGCACACAGGTGCTGCATGGCTGTCGTC AGCTCGTGTCGTGAGATGTTGGGTTAAGT CCCGCAACGAGCGCAACCCACGTCCTTAG TTGCCATCATTCAGTTGGGCACTCTAGGG AGACTGCCGGTGATAAGCCGCGAGGAAG GTGTGGATGACGTCAAGTCCTCATGGCCC TTACGGGATGGGCTACACACGTGCTACAA TGGCGGTGACAGTGGGACGCGAAACCGC GAGGTTGAGCAAATCCCCAAAAGCCGTCT |

TABLE 1-continued

16S RNA encoding sequences

| Isolate (NLS No.) | SEQ ID NO: | DNA sequence encoding the 16S RNA |
|---|---|---|
| | | CAGTTCGGATTGCACTCTGCAACTCGGGT GCATGAAGGCGGAATCGCTAGTAATCGT GGATCAGCACGCCACGGTGAATACGTTCC CGGGCCTTGTACACACCGCCCGTCACACC ATGGGAGTTGGTCTTACCCGACGGCGCTG CGCCAACCGCAAGGGGGCAGGCGACCAC GGTAGGGTCAGCGACTGGGGTGAAGTCG TAACAAGGTAGCCGTAGGGGAACCTGCG GCTGGATCACCT |

Various *Methylobacterium* sp. isolates provided herein are disclosed in Table 2.

TABLE 2

*Methylobacterium* sp. Isolates

| NLS No. | Plant host of original isolate | USDA ARS NRRL No.[1] |
|---|---|---|
| NLS0021 | lettuce | NRRL B-50939 |
| NLS0038 | tomato | NRRL B-50942 |
| NLS0042 | soybean | NRRL B-50932 |
| NLS0934 | soybean | NRRL B-67341[1] (Received by Depository on Nov. 18, 2016[2]) |
| NLS0062 | corn | NRRL B-50937 |
| NLS0069 | corn | NRRL B-50936 |
| NLS0089 | broccoli | NRRL B-50933 |
| NLS0037 | | NRRL B-50941 |

[1]Deposit number for strains deposited with the AGRICULTURAL RESEARCH SERVICE CULTURE COLLECTION (NRRL) of the National Center for Agricultural Utilization Research, Agricultural Research Service, U.S. Department of Agriculture, 1815 North University Street, Peoria, Illinois 61604 U.S.A. under the terms of the Budapest Treaty on the International Recognition of the Deposit of Microorganisms for the Purposes of Patent Procedure. Subject to 37 CFR §1.808(b), all restrictions imposed by the depositor on the availability to the public of the deposited material will be irrevocably removed upon the granting of any patent from this patent application.

Also provided herein are methods for controlling RLN that comprise applying any of the aforementioned compositions provided herein to a plant or a plant part in an amount that provides for inhibition of RLN damage in the plant, plant part, or a plant obtained therefrom relative to infection of, or damage in, a control plant, plant part, or plant obtained therefrom that had not received an application of the composition. In certain embodiments, application of the composition provides for at least about 5%, at least about 10%, at least about 20%, at least about 30%, at least about 40%, at least about 50%, at least about 75%, at least about 85%, or at least about 95% reduction of RLN damage in the plant, plant part, or a plant derived therefrom relative to RLN damage of the control plant, plant part, or plant obtained therefrom. In certain embodiments, application of the composition provides for at least about 5%, at least about 10%, at least about 20%, at least about 30%, at least about 40%, at least about 50%, at least about 75%, at least about 85%, or at least about 95% reduction of RLN reproduction, viability, or motility in the plant, plant part, or a plant derived therefrom relative to RLN reproduction, viability, or motility in the control plant, plant part, or plant obtained therefrom. In certain embodiments, application of the composition provides for at least about 5%, at least about 10%, at least about 20%, at least about 30%, at least about 40%, at least about 50%, at least about 75%, at least about 85%, or at least about 95% reduction of RLN recovered from the plant, plant part, or a plant derived therefrom relative to RLN recovered from the control plant, plant part, or plant obtained therefrom. In certain embodiments, the methods provide for a decrease in numbers of RLN obtained from the treated plant, plant part, or a plant derived therefrom relative to an untreated control plant, plant part, or a plant derived therefrom. In certain embodiments, application of the composition provides for at least about 5%, at least about 10%, at least about 20%, at least about 30%, at least about 40%, at least about 50%, at least about 75%, at least about 85%, or at least about 95% reduction of RLN populations in soil. In certain embodiments, the plant part is selected from the group consisting of a leaf, a stem, a flower, a root, a tuber, a pollen grain, and a seed. In certain embodiments, the method further comprises the step of harvesting at least one plant part selected from the group consisting of a leaf, a stem, a flower, a root, a tuber, a pollen grain, or a seed from the plant or plant part. In certain embodiments of any of the aforementioned methods, the methods further comprise obtaining a processed food or feed composition from the plant or plant part. In certain embodiments, the processed food or feed composition is a meal or a paste. In certain embodiments of any of the aforementioned methods, the RLN-inhibitory *Methylobacterium* is selected from the group consisting of *Methylobacterium* NLS0021, NLS0038, NLS0042, NLS0934, NLS0062, NLS0069, NLS0089, derivatives thereof, and *Methylobacterium* related thereto. In certain embodiments, the RLN-inhibitory *Methylobacterium* is selected from the group consisting of *Methylobacterium* NLS0021, NLS0038, NLS0069, and a derivative thereof.

Also provided are methods of making the compositions useful for controlling RLN that comprise combining at least one of a RLN-inhibitory *Methylobacterium*, a RLN-inhibitory cell-free culture supernatant, fraction thereof, concentrate thereof, or any combination thereof with an agriculturally acceptable excipient and/or with an agriculturally acceptable adjuvant. In certain embodiments of the methods, the *Methylobacterium* is adhered to a solid substance. In certain embodiments of the methods, the *Methylobacterium* is adhered to the solid substance is combined with a liquid to form a composition that is a colloid. In certain embodiments of the methods, the colloid is a gel. In certain embodiments of the methods, the *Methylobacterium* adhered to the solid substance is provided by culturing the *Methylobacterium* in the presence of the solid substance. In certain embodiments of the methods, the composition comprises an emulsion. In certain embodiments of the methods, the *Methylobacterium* is provided by culturing the *Methylobacterium* in an emulsion. In certain embodiments of any of the aforementioned methods, the RLN-inhibitory *Methylobacterium* is selected from the group consisting of *Methylobacterium* NLS0021, NLS0038, NLS0042, NLS0934, NLS0062, NLS0069, NLS0089, derivatives thereof, and *Methylobacterium* related thereto. In certain embodiments, the RLN-inhibitory *Methylobacterium* is selected from the group consisting of *Methylobacterium* NLS0021, NLS0038, NLS0069, and a derivative thereof.

Methods where *Methylobacterium* are cultured in biphasic media comprising a liquid phase and a solid substance have been found to significantly increase the resultant yield of *Methylobacterium* relative to methods where the *Methylobacterium* are cultured in liquid media alone. In certain embodiments, the methods can comprise growing the *Methylobacterium* in liquid media with a particulate solid substance that can be suspended in the liquid by agitation under conditions that provide for *Methylobacterium* growth. In certain embodiments where particulate solid substances are used, at least substantially all of the solid phase can thus be suspended in the liquid phase upon agitation. Such particulate solid substances can comprise materials that are about 1 millimeter or less in length or diameter. In certain embodiments, the degree of agitation is sufficient to provide for uniform distribution of the particulate solid substance in the liquid phase and/or optimal levels of culture aeration. However, in other embodiments provided herein, at least substantially all of the solid phase is not suspended in the liquid phase, or portions of the solid phase are suspended in the liquid phase and portions of the solid phase are not suspended in the liquid phase. Non-particulate solid substances can be used in certain biphasic media where the solid phase is not suspended in the liquid phase. Such non-particulate solid substances include, but are not limited to, materials that are greater than about 1 millimeter in length or diameter. Such particulate and non-particulate solid substances also include, but are not limited to, materials that are porous, fibrous, or otherwise configured to provide for increased surface areas for adherent growth of the *Methylobacterium*. Biphasic media where portions of the solid phase are suspended in the liquid phase and portions of the solid phase are not suspended in the liquid phase can comprise a mixture of particulate and non-particulate solid substances. Such particulate and non-particulate solid substances used in any of the aforementioned biphasic media also include, but are not limited to, materials that are porous, fibrous, or otherwise configured to provide for increased surface areas for adherent growth of the *Methylobacterium*. In certain embodiments, the media comprises a colloid formed by a solid and a liquid phase. A colloid comprising a solid and a liquid can be pre-formed and added to liquid media or can be formed in media containing a solid and a liquid. Colloids comprising a solid and a liquid can be formed by subjecting certain solid substances to a chemical and/or thermal change. In certain embodiments, the colloid is a gel. In certain embodiments, the liquid phase of the media is an emulsion. In certain embodiments, the emulsion comprises an aqueous liquid and a liquid that is not miscible, or only partially miscible, in the aqueous liquid. Liquids that are not miscible, or only partially miscible, in water include, but are not limited to, any of the following: (1) liquids having a miscibility in water that is equal to or less than that of pentanol, hexanol, or heptanol at 25 degrees C.; (2) liquids comprising an alcohol, an aldehyde, a ketone, a fatty acid, a phospholipid, or any combination thereof; (3) alcohols selected from the group consisting of aliphatic alcohols containing at least 5 carbons and sterols; (4) an animal oil, microbial oil, synthetic oil, plant oil, or combination thereof; and/or, (5) a plant oil is selected from the group consisting of, soybean, cotton, peanut, sunflower, olive, flax, coconut, palm, rapeseed, sesame seed, safflower, and combinations thereof. In certain embodiments, the immiscible or partially immiscible liquid can comprises at least about 0.02% to about 20% of the liquid phase by mass. In certain embodiments, the methods can comprise obtaining a biphasic culture media comprising the liquid, the solid, and *Methylobacterium* and incubating the culture under conditions that provide for growth of the *Methylobacterium*. Biphasic culture medias comprising the liquid, the solid, and *Methylobacterium* can be obtained by a variety of methods that include, but are not limited to, any of: (a) inoculating a biphasic media comprising the liquid and the solid substance with *Methylobacterium*; (b) inoculating the solid substance with *Methylobacterium* and then introducing the solid substance comprising the *Methylobacterium* into the liquid media; (c) inoculating the solid substance with *Methylobacterium*, incubating the *Methylobacterium* on the solid substance, and then introducing the solid substance comprising the *Methylobacterium* into the liquid media; or (d) any combination of (a), (b), or (c). Methods and compositions for growing *Methylobacterium* in biphasic media comprising a liquid and a solid are disclosed in co-assigned U.S. Pat. No. 9,181,541, issued Nov. 10, 2015, which is incorporated herein by reference in its entirety. Compositions comprising dried formulations of *Methylobacterium* that are adhered to solid substances, methods for making such compositions, and methods of applying those compositions to plants and plant parts including seeds are disclosed in co-assigned U.S. patent application Ser. No. 14/856,020, filed Sep. 16, 2015, and which is incorporated herein by reference in its entirety.

Methods where *Methylobacterium* are cultured in media comprising an emulsion have also been found to significantly increase the resultant yield of *Methylobacterium* relative to methods where the *Methylobacterium* are cultured in liquid media alone. In certain embodiments, the methods for making the compositions provided herein can comprise growing the RLN-inhibitory *Methylobacterium* agent in an emulsion under conditions that provide for *Methylobacterium* growth. Media comprising the emulsion and RLN-inhibitory *Methylobacterium* can be obtained by a variety of methods that include, but are not limited to, any of: (a) inoculating a media comprising the emulsion with *Methylobacterium*; (b) inoculating the aqueous liquid with the *Methylobacterium*, introducing the non-aqueous liquid, and mixing to form an emulsion; (c) inoculating the aqueous liquid with the *Methylobacterium*, introducing the non-aqueous liquid, and mixing to form an emulsion; or (d) any combination of (a), (b), or (c). In certain embodiments, the emulsion comprises an aqueous liquid and a liquid that is not miscible, or only partially miscible, in the aqueous liquid. Non-aqueous liquids that are not miscible, or only partially miscible, in water include, but are not limited to, any of the following: (1) liquids having a miscibility in water that is equal to or less than that of n-pentanol, n-hexanol, or n-heptanol at 25 degrees C.; (2) liquids comprising an alcohol, an aldehyde, a ketone, a fatty acid, a phospholipid, or any combination thereof (3) alcohols is selected from the group consisting of aliphatic alcohols containing at least 5, 6, or 7 carbons and sterols; (4) an animal oil, microbial oil, synthetic oil, plant oil, or combination thereof; and/or, (5) a plant oil is selected from the group consisting of, soybean, cotton, peanut, sunflower, olive, flax, coconut, palm, rapeseed, sesame seed, safflower, and combinations thereof. In certain embodiments, the immiscible or partially immiscible non-aqueous liquid can comprise at least about 0.02% to about 20% of the emulsion by mass. In certain embodiments, the immiscible or partially immiscible non-aqueous liquid can comprise at least about any of about 0.05%, 0.1%, 0.5%, or 1% to about 3%, 5%, 10%, or 20% of the emulsion by mass. Methods and compositions for growing *Methylobacterium* in media comprising an emulsion are disclosed in co-assigned International Patent Application PCT/US14/40218, filed May 30, 2014, and US Patent Application Publication No. 20160120188, which is incorporated herein by reference in its entirety.

In certain embodiments, compositions that comprise at least one of a RLN-inhibitory *Methylobacterium*, a RLN-inhibitory cell-free culture supernatant, fraction thereof, concentrate thereof, or any combination thereof can further comprise one or more introduced microorganisms of pre-determined identity other than *Methylobacterium*. Other microorganisms that can be added include, but are not limited to, microorganisms that are biopesticidal or provide some other benefit when applied to a plant or plant part. Biopesticidal or otherwise beneficial microorganisms thus include, but are not limited to, various *Bacillus* sp., *Pseudomonas* sp., *Coniothyrium* sp., *Pantoea* sp., *Streptomyces* sp., and *Trichoderma* sp. Microbial biopesticides can be a *bacterium*, fungus, virus, or protozoan. Particularly useful biopesticidal microorganisms include various *Bacillus subtilis, Bacillus thuringiensis, Bacillus pumilis* (e.g., *Bacillus pumilis* strain QST2808), *Pseudomonas syringae, Trichoderma harzianum, Trichoderma vixens*, and *Streptomyces lydicus* strains. Biopesticidal microorganisms that can be used include, but are not limited to, the *Bacillus pumilis* strains described in U.S. Pat. No. 9,023,339, and the *Bacillus cereus* and *Bacillus firmus* strains disclosed in U.S. Pat. No. 6,406,690, each of which are incorporated herein by reference in their entireties. Other microorganisms that are added can be genetically engineered or other isolates that are available as pure cultures. In certain embodiments, it is anticipated that the bacterial or fungal microorganism can be provided in the fermentation broth, fermentation broth product, or composition in the form of a spore.

In certain embodiments, a RLN-inhibitory *Methylobacterium*, a RLN-inhibitory cell-free culture supernatant, fraction thereof, concentrate thereof, or any combination thereof that are provided herein can be used in conjunction with transgenic plants that express gene products that are inhibitory to growth of certain RLN. Such transgenic plants include, but are not limited to, those expressing interfering RNA molecules that suppress endogenous RLN genes such as those disclosed in U.S. Patent Appl. Publication No. US 20150135363, which is incorporated herein by reference in its entirety.

In certain embodiments, the compositions comprising at least one of a RLN-inhibitory *Methylobacterium*, a RLN-inhibitory cell-free culture supernatant, fraction thereof, concentrate thereof, or any combination thereof that are provided herein can be used in conjunction with plants that comprise one or more genetic loci that can confer resistance to RLN. Such RLN resistant plants include, but are not limited to, wheat plants comprising the Rlnn1 gene (Theoretical and Applied Genetics, 2002, 104 (5): 874-879) or alfalfa plants (Baldridge et al. Plant Molecular Biology, 1998, 38(6): 999-1010).

In certain embodiments, the compositions comprising at least one of a RLN-inhibitory *Methylobacterium*, a RLN-inhibitory cell-free culture supernatant, fraction thereof, concentrate thereof, or any combination thereof that are provided herein can be used in conjunction with, or comprise, nematicides that also provide for inhibition of RLN growth and/or reproduction and/or reductions in RLN-mediated plant damage. Such nematicides can be used in soil treatments (drenches, in furrow deposits, and the like) and/or in seed treatments. In certain embodiments, the nematicide is selected from the group consisting of organophosphate, biological, and carbamate nematicides. In certain embodiments, the seed is treated with one or more of the aforementioned nematicides (U.S. Pat. Nos. 6,660,690 and 8,080, 496, each incorporated herein by reference in their entireties). Commercial soil applied nematicide formulations that can be used in conjunction with the RLN-inhibitory *Methylobacterium* sp. provided herein include, but are not limited to, formulations containing the carbamates aldicarb, aldoxycarb, oxamyl, carbofuran, and cleothocarb, and/ or the organophosphates thionazin, ethoprophos, fenamiphos, fensulfothion, and/or terbufos formulations. Combinations of the aforementioned nematicides and the aforementioned transgenic plants that provide for inhibition of RLN growth and/or reproduction and/or reductions in RLN-mediated plant damage can also be used in conjunction with the RLN-inhibitory *Methylobacterium* sp. provided herein.

In certain embodiments, any of the aforementioned compositions comprising RLN-inhibitory *Methylobacterium* sp., a RLN-inhibitory cell-free culture supernatant, fraction thereof, concentrate thereof, or any combination thereof that are provided herein are selectively applied to plant parts or to soil or other media in which a plant is or is to be grown, or plant parts subjected to such applications are used in soil or media, following a determination that RLN levels in the soil or other media in which the plants are grown are above levels that would result in RLN damage in the absence of such applications or use. Soil or media in which the plant is to be grown can be surveyed for the presence of RLN and the composition is applied to the plant part, soil, or media when the RLN are present in the soil or media at a level that can result in reductions in plant growth, yield, water-deficit tolerance, chlorosis, produce quality, and combinations thereof to an untreated control plant. In certain embodiments, the composition is not applied to the plant part, soil, or media when the RLN are present in the soil or media below levels that can result in reductions in plant growth, yield, water-deficit tolerance, chlorosis, produce quality, and combinations thereof to an untreated control plant. Any survey method that provides for a determination of RLN levels that result in plant damage can be used. In certain embodiments, plants having yellow lower leaves and loss of secondary branching in the root system that are found in patches in a field can indicate that RLN are present (Johnson et al. Root Lesion Nematodes in Wheat, Mont. State University Extension Publication MT200801AG, February 2008) and prompt use of the compositions provided herein. In other embodiments, samples are taken from the soil or media in which the plants are to be grown and levels of RLN are determined (Todd et al. Plant Health Progress 15(3):112, 2014). In certain embodiments where the RLN are present in soil above threshold levels that result in yield loss, the compositions provided herein are used.

In certain embodiments, the liquid medium that can be used in the methods and compositions that provide for the efficient growth of *Methylobacterium* is prepared from inexpensive and readily available components, including, but not limited to, inorganic salts such as potassium phosphate, magnesium sulfate and the like, carbon sources such as glycerol, methanol, glutamic acid, aspartic acid, succinic acid and the like, and amino acid blends such as peptone, tryptone, and the like. Non-limiting examples of liquid media that can be used include, but are not limited to, ammonium mineral salts (AMS) medium (Whittenbury et al., 1970), Vogel-Bonner (VB) minimal culture medium (Vogel and Bonner, 1956), and LB broth ("Luria-Bertani Broth").

In general, the solid substance that can in certain embodiments be used in the methods and compositions that provide for the efficient growth of *Methylobacterium* can be any suitable solid substance which is insoluble or only partially soluble in water or aqueous solutions. Such suitable solid substances are also non-bacteriocidal or non-bacteriostatic with respect to RLN-inhibitory *Methylobacterium* sp. when the solid substances are provided in the liquid culture media. In certain embodiments, such suitable solid substances are also solid substances that are readily obtained in sterile form or rendered sterile. Solid substances used herein can be sterilized by any method that provides for removal of contaminating microorganisms and thus include, but are not limited to, methods such as autoclaving, irradiation, chemical treatment, and any combination thereof. These solid substances include substances of animal, plant, microbial, fungal, or mineral origin, manmade substances, or combinations of substances of animal, plant, microbial, fungal, or mineral origin and manmade substances. In certain embodiments, the solid substances are inanimate solid substances. Inanimate solid substances of animal, plant, microbial, or fungal origin can be obtained from animals, plants, microbes, or fungi that are inviable (i.e. no longer living) or that have been rendered inviable. Diatom shells are thus inanimate solid substances when previously associated diatom algae have been removed or otherwise rendered inviable. Since diatom shells are inanimate solid substances, they are not considered to be photosynthetic organisms or photosynthetic microorganisms. In certain embodiments, solid substances include, but are not limited to, sand, silt, soil, clay, ash, charcoal, diatomaceous earth and other similar minerals, ground glass or glass beads, ground ceramic materials, ceramic beads, bentonite, kaolin, talc, perlite, mica, vermiculite, silicas, quartz powder, montmorillonite, and combinations thereof. In certain embodiments, the solid substance can be a polymer or polymeric beads. Polymers that can be used as a solid substance include, but are not limited to, various polysaccharides such as cellulosic polymers and chitinous polymers which are insoluble or only partially soluble in water or aqueous solutions, agar (i.e. galactans), and combinations thereof. In certain embodiments, the solid substance can be an insoluble or only partially soluble salt crystal. Salt crystals that can be used include, but are not limited to, insoluble or only partially soluble carbonates, chromates, sulfites, phosphates, hydroxides, oxides, and sulfides. In certain embodiments, the solid substance can be a microbial cell, fungal cell, microbial spore, or fungal spore. In certain embodiments, the solid substance can be a microbial cell or microbial spore wherein the microbial cell or microbial spore is not a photosynthetic microorganism. In still other embodiments, the solid substance can be an inactivated (i.e. inviable) microbial cell, fungal cell, microbial spore, or fungal spore. In still other embodiments, the solid substance can be a quiescent (i.e. viable but not actively dividing) microbial cell, fungal cell, microbial spore, or fungal spore. In still other embodiments, the solid substance can be cellular debris of microbial origin. In still other embodiments, the solid substance can be particulate matter from any part of a plant. Plant parts that can be used to obtain the solid substance include, but are not limited to, cobs, husks, hulls, leaves, roots, flowers, stems, barks, seeds, and combinations thereof. Products obtained from processed plant parts including, but not limited to, bagasse, wheat bran, soy grits, crushed seed cake, stover, and the like can also be used. Such plant parts, processed plants, and/or processed plant parts can be milled to obtain the solid material in a particulate form that can be used. In certain embodiments, wood or a wood product including, but not limited to, wood pulp, sawdust, shavings, and the like can be used. In certain embodiments, the solid substance can be a particulate matter from an animal(s), including, but not limited to, bone meal, gelatin, ground or powdered shells, hair, macerated hide, and the like.

In certain embodiments, the solid substance is provided in a particulate form that provides for distribution of the solid substance in the culture media. In certain embodiments, the solid substance is comprised of particle of about 2 microns to about 1000 microns in average length or average diameter. In certain embodiments, the solid substance is comprised of particle of about 1 microns to about 1000 microns in average length or average diameter. In certain embodiments, the solid substance is a particle of about 1, 2, 4, 10, 20, or 40 microns to any of about 100, 200, 500, 750, or 1000 microns in average length or average diameter. Desirable characteristics of particles used in the methods and compositions provided herein include suitable wettability such that the particles can be suspended throughout the media upon agitation.

In certain embodiments, the solid substance is provided in the media as a colloid wherein the continuous phase is a liquid and the dispersed phase is the solid. Suitable solids that can be used to form colloids in liquid media used to grow RLN-inhibitory *Methylobacterium* sp. include, but are not limited to, various solids that are referred to as hydrocolloids. Such hydrocolloids used in the media, methods and compositions provided herein can be hydrophilic polymers, of plant, animal, microbial, or synthetic origin. Hydrocolloid polymers used in the methods can contain many hydroxyl groups and/or can be polyelectrolytes. Hydrocolloid polymers used in the compositions and methods provided herein include, but are not limited to, agar, alginate, arabinoxylan, carrageenan, carboxymethylcellulose, cellulose, curdlan, gelatin, gellan, β-glucan, guar gum, gum arabic, locust bean gum, pectin, starch, xanthan gum, and mixtures thereof. In certain embodiments, the colloid used in the media, methods, and compositions provided herein can comprise a hydrocolloid polymer and one or more proteins.

In certain embodiments, the solid substance can be a solid substance that provides for adherent growth of the RLN-inhibitory *Methylobacterium* sp. on the solid substance. RLN-inhibitory *Methylobacterium* sp. that are adhered to a solid substance are *Methylobacterium* that cannot be substantially removed by simply washing the solid substance with the adherent RLN-inhibitory *Methylobacterium* sp. with growth media whereas non-adherent *Methylobacterium* can be substantially removed by washing the solid substance with liquid growth media. In this context, "substantially removed" means that at least about 30%, 40%, 50%, 60%, 70%, or 80% the *Methylobacterium* present are removed when the solid substance is washed with three volumes of liquid growth media. Such washing can be effected by a variety of methods including, but not limited to, decanting liquid from a washed solid phase or passing liquid through a solid phase on a filter that permits flow through of bacteria in the liquid. In certain embodiments, the adherent RLN-inhibitory *Methylobacterium* sp. that are associated with the solid can include both *Methylobacterium* that are directly attached to the solid and/or *Methylobacterium* that are indirectly attached to the solid substance. *Methylobacterium* that are indirectly attached to the solid substance include, but are not limited to, *Methylobacterium* that are attached to another *Methylobacterium* or to another microorganism that is attached to the solid substance, *Methylobacterium* that are attached to the solid substance by being attached to another substance that is attached to the solid substance, and the like. In certain embodiments, at least 10%, 20%, 30%, 40%, 50%, 60%, 70%, 80%, 90%, 95%, 98%, 99%, 99.5% or 99.9% of the *Methylobacterium* in the fermentation broth, fermentation broth product, or compositions are *Methylobacterium* that are adhered to the solid substance. In certain embodiments, adherent RLN-inhibitory *Methylobacterium* sp. can be present on the surface of the solid substance in the fermentation broth, fermentation broth product, or composition at a density of at least about 1 *Methylobacterium*/20 square micrometers, of at least about 1 *Methylobacterium*/10 square micrometers, of at least about 1 *Methylobacterium*/10 square micrometers, of at least about 1 *Methylobacterium*/5 square micrometers, of at least about 1 *Methylobacterium*/2 square micrometers, or of at least about 1 *Methylobacterium*/square micrometer. In certain embodiments, adherent RLN-inhibitory *Methylobacterium* sp. can be present on the surface of the solid substance in the fermentation broth, fermentation broth product, or composition at a density of at least about 1 *Methylobacterium*/20 square micrometers to about 1 *Methylobacterium*/square micrometer, of at least about 1 *Methylobacterium*/10 square micrometers to about 1 *Methylobacterium*/square micrometer, of at least about 1 *Methylobacterium*/10 square micrometers to about 1 *Methylobacterium*/square micrometer, of at least about 1 *Methylobacterium*/5 square micrometers to about 1 *Methylobacterium*/square micrometer, or of at least about 1 *Methylobacterium*/2 square micrometers to about 1 *Methylobacterium*/square micrometer. In certain embodiments, adherent RLN-inhibitory *Methylobacterium* sp. can be present on the surface of the solid substance in the fermentation broth, fermentation broth product, or composition at a density of at least about 1 *Methylobacterium*/20 square micrometers to about 1 *Methylobacterium*/2 square micrometers, of at least about 1 *Methylobacterium*/10 square micrometers to about 1 *Methylobacterium*/2 square micrometers, of at least about 1 *Methylobacterium*/10 square micrometers to about 1 *Methylobacterium*/2 square micrometers, or of at least about 1 *Methylobacterium*/5 square micrometers to about 1 *Methylobacterium*/2 square micrometers. Biphasic fermentation broths provided herein can comprise a liquid phase that contains non-adherent *Methylobacterium*. In certain embodiments, titers of non-adherent *Methylobacterium* in the liquid phase can be less than about 100,000, 10,000, or 1,000 CFU/ml. In certain embodiments, the RLN-inhibitory *Methylobacterium* is selected from the group consisting of *Methylobacterium* NLS0021, NLS0038, NLS0042, NLS0934, NLS0062, NLS0069, NLS0089, derivatives thereof, and *Methylobacterium* related thereto. In certain embodiments, the RLN-inhibitory *Methylobacterium* is selected from the group consisting of *Methylobacterium* NLS0037 and a derivative thereof.

Biphasic culture methods provided can yield fermentation broths with RLN-inhibitory *Methylobacterium* sp. at a titer of greater than about $5\times10^8$ colony-forming units per milliliter, at a titer of greater than about $1\times10^9$ colony-forming units per milliliter, at a titer of greater than about $1\times10^{10}$ colony-forming units per milliliter, at a titer of at least about $3\times10^{10}$ colony-forming units per milliliter. In certain embodiments, fermentation broths provided herein can comprise RLN-inhibitory *Methylobacterium* sp. at a titer of at least about $5\times10^8$ colony-forming units per milliliter to at least about $3\times10^{10}$ colony-forming units per milliliter, at least about $5\times10^8$ colony-forming units per milliliter to at least about $4\times10^{10}$ colony-forming units per milliliter, or at least about $5\times10^8$ colony-forming units per milliliter to at least about $6\times10^{10}$ colony-forming units per milliliter. In certain embodiments, fermentation broths provided herein can comprise RLN-inhibitory *Methylobacterium* sp. at a titer of at least about $1\times10^9$ colony-forming units per milliliter to at least about $3\times10^{10}$ colony-forming units per milliliter, at least about $1\times10^9$ colony-forming units per milliliter to at least about $4\times10^{10}$ colony-forming units per milliliter, or at least about $1\times10^9$ colony-forming units per milliliter to at least about $6\times10^{10}$ colony-forming units per milliliter. In certain embodiments, fermentation broths provided herein will comprise RLN-inhibitory *Methylobacterium* sp. at a titer of at least about $1\times10^{10}$ colony-forming units per milliliter to at least about $3\times10^{10}$ colony-forming units per milliliter, at least about $1\times10^{10}$ colony-forming units per milliliter to at least about $4\times10^{10}$ colony-forming units per milliliter, or at least about $1\times10^{10}$ colony-forming units per milliliter to at least about $6\times10^{10}$ colony-forming units per milliliter. In certain embodiments, fermentation broths provided herein will comprise RLN-inhibitory *Methylobacterium* sp. at a titer of, at least about $3\times10^{10}$ colony-forming units per milliliter to at least about $4\times10^{10}$ colony-forming units per milliliter, or at least about $3\times10^{10}$ colony-forming units per milliliter to at least about $6\times10^{10}$ colony-forming units per milliliter. In certain embodiments, the RLN-inhibitory *Methylobacterium* is selected from the group consisting of *Methylobacterium* NLS0021, NLS0038, NLS0042, NLS0934, NLS0062, NLS0069, NLS0089, derivatives thereof, and *Methylobacterium* related thereto. In certain embodiments, the RLN-inhibitory *Methylobacterium* is selected from the group consisting of *Methylobacterium* NLS0021, NLS0038, NLS0069, and a derivative thereof.

Solid substances with adherent RLN-inhibitory *Methylobacterium* sp. obtained as fermentation products can be used to make various compositions useful for treating plants or plant parts to inhibit RLN growth and/or reproduction or reduce RLN damage to a plant. Such compositions can comprise at least one of a RLN-inhibitory *Methylobacterium* sp., a solid substance with adherent RLN-inhibitory *Methylobacterium* sp., a RLN-inhibitory cell-free culture supernatant, fraction thereof, concentrate thereof, or any combination thereof. Compositions provided herein comprising RLN-inhibitory *Methylobacterium* sp., solid substances with RLN-inhibitory *Methylobacterium* sp. grown thereon, or comprising emulsions with RLN-inhibitory *Methylobacterium* sp. grown therein can be used to treat plants or plant parts. Plants, plant parts, and, in particular, plant seeds that have been at least partially coated or coated with the aforementioned compositions are thus provided. Also provided are processed plant products that contain any of the aforementioned compositions. Solid substances with adherent RLN-inhibitory *Methylobacterium* sp. can be used to make various compositions that are particularly useful for treating plant seeds. Seeds that have been at least partially coated with any of the aforementioned compositions are thus provided. Also provided are processed seed products, including, but not limited to, meal, flour, feed, and flakes that contain the fermentation broth products or compositions provided herein. In certain embodiments, the processed plant product will be non-regenerable (i.e. will be incapable of developing into a plant). In certain embodiments, the solid substance used in the fermentation product or composition that at least partially coats the plant, plant part, or plant seed or that is contained in the processed plant, plant part, or seed product comprises a solid substance and associated or adherent RLN-inhibitory *Methylobacterium* sp. that can be readily identified by comparing a treated and an untreated plant, plant part, plant seed, or processed product thereof. In certain embodiments, the RLN-inhibitory *Methylobacterium* is selected from the group consisting of *Methylobacterium* NLS0021, NLS0038, NLS0042, NLS0934, NLS0062, NLS0069, NLS0089, derivatives thereof, and *Methylobacterium* related thereto. In certain embodiments, the RLN-inhibitory *Methylobacterium* is selected from the group consisting of *Methylobacterium* NLS0021, NLS0038, NLS0069, and a derivative thereof.

Compositions useful for treating plants or plant parts that comprise at least one of a RLN-inhibitory *Methylobacterium* sp., a solid substance with adherent RLN-inhibitory *Methylobacterium* sp., emulsions with RLN-inhibitory *Methylobacterium* sp. grown therein, a RLN-inhibitory cell-free culture supernatant, fraction thereof, concentrate thereof, or any combination thereof, can also further comprise an agriculturally acceptable adjuvant or an agriculturally acceptable excipient. Such compositions can be in a liquid or dry form. An agriculturally acceptable adjuvant or an agriculturally acceptable excipient is typically an ingredient that does not cause undue phytotoxicity or other adverse effects when exposed to a plant or plant part. In certain embodiments, the solid substance can itself be an agriculturally acceptable adjuvant or an agriculturally acceptable excipient so long as it is not bacteriocidal or bacteriostatic to the Methylobacterium. In other embodiments, the composition further comprises at least one of an agriculturally acceptable adjuvant or an agriculturally acceptable excipient. Any of the aforementioned compositions can also further comprise a pesticide. Pesticides used in the composition include, but are not limited to, a nematicide, a fungicide, and a bacteriocide. In certain embodiments, the pesticide used in the composition is a pesticide that does not substantially inhibit growth of the Methylobacterium. As Methylobacterium are gram negative bacteria, suitable bacteriocides used in the compositions can include, but are not limited to, bacteriocides that exhibit activity against gram positive bacteria but not gram negative bacteria. Compositions provided herein can also comprise a bacteriostatic agent that does not substantially inhibit growth of the Methylobacterium. Bacteriostatic agents suitable for use in compositions provided herein include, but are not limited to, those that exhibit activity against gram positive bacteria but not gram negative bacteria. Any of the aforementioned compositions can also be an essentially dry product (i.e. having about 5% or less water content), a mixture of the composition with an emulsion, or a suspension.

Agriculturally acceptable adjuvants used in the compositions that comprise at least one of a RLN-inhibitory Methylobacterium sp., a solid substance with adherent RLN-inhibitory Methylobacterium sp., emulsions with RLN-inhibitory Methylobacterium sp. grown therein, a RLN-inhibitory cell-free culture supernatant, fraction thereof, concentrate thereof, or any combination thereof include, but are not limited to, components that enhance product efficacy and/or products that enhance ease of product application. Adjuvants that enhance product efficacy can include various wetters/spreaders that promote adhesion to and spreading of the composition on plant parts, stickers that promote adhesion to the plant part, penetrants that can promote contact of the active agent with interior tissues, extenders that increase the half-life of the active agent by inhibiting environmental degradation, and humectants that increase the density or drying time of sprayed compositions. Wetters/spreaders used in the compositions can include, but are not limited to, non-ionic surfactants, anionic surfactants, cationic surfactants, amphoteric surfactants, organo-silicate surfactants, and/or acidified surfactants. Stickers used in the compositions can include, but are not limited to, latex-based substances, terpene/pinolene, and pyrrolidone-based substances. Penetrants can include mineral oil, vegetable oil, esterified vegetable oil, organo-silicate surfactants, and acidified surfactants. Extenders used in the compositions can include, but are not limited to, ammonium sulphate, or menthene-based substances. Humectants used in the compositions can include, but are not limited to, glycerol, propylene glycol, and diethyl glycol. Adjuvants that improve ease of product application include, but are not limited to, acidifying/buffering agents, anti-foaming/de-foaming agents, compatibility agents, drift-reducing agents, dyes, and water conditioners. Anti-foaming/de-foaming agents used in the compositions can include, but are not limited to, dimethopolysiloxane. Compatibility agents used in the compositions can include, but are not limited to, ammonium sulphate. Drift-reducing agents used in the compositions can include, but are not limited to, polyacrylamides, and polysaccharides. Water conditioners used in the compositions can include, but are not limited to, ammonium sulphate.

Methods of treating plants and/or plant parts with the compositions comprising at least one of a RLN-inhibitory Methylobacterium sp., a solid substance with adherent RLN-inhibitory Methylobacterium sp., emulsions with RLN-inhibitory Methylobacterium sp. grown therein, a RLN-inhibitory cell-free culture supernatant, fraction thereof, concentrate thereof, or any combination thereof are also provided herein. Treated plants, and treated plant parts obtained therefrom, include, but are not limited to, Brassica sp. (e.g., B. napus, B. rapa, B. juncea), corn, wheat, rye, rice, alfalfa, rice, rye, sorghum, millet (e.g., pearl millet (Pennisetum glaucum), proso millet (Panicum miliaceum), foxtail millet (Setaria italica), finger millet (Eleusine coracana), sunflower, safflower, soybean, tobacco, potato, peanuts, carrot, cotton, sweet potato (Ipomoea batatus), cassava, coffee, coconut, pineapple, citrus trees, cocoa, tea, banana, avocado, fig, guava, mango, olive, papaya, cashew, macadamia, almond, sugar beets, sugarcane, strawberry, oats, barley, tomato, lettuce, pepper, green beans, lima beans, peas, cucurbits such as cucumber, cantaloupe, and musk melon, turf, ornamentals, and conifers. Plant parts that are treated include, but are not limited to, leaves, stems, flowers, roots, seeds, fruit, tubers, coleoptiles, and the like. Ornamental plants and plant parts that can be treated include, but are not limited to azalea, hydrangea, hibiscus, roses, tulips, daffodils, petunias, carnation, poinsettia, and chrysanthemum. Seeds or other propagules of any of the aforementioned plants can be treated with the fermentation broths, fermentation broth products, fermentation products, and/or compositions provided herein.

In certain embodiments, plants and/or plant parts are treated by applying compositions that comprise at least one of a RLN-inhibitory Methylobacterium sp., a solid substance with adherent RLN-inhibitory Methylobacterium sp., emulsions with RLN-inhibitory Methylobacterium sp. grown therein, a RLN-inhibitory cell-free culture supernatant, fraction thereof, concentrate thereof, or any combination thereof as a spray. Such spray applications include, but are not limited to, treatments of a single plant part or any combination of plant parts. Spraying can be achieved with any device that will distribute the fermentation broths, fermentation broth products, fermentation products, and compositions to the plant and/or plant part(s). Useful spray devices include a boom sprayer, a hand or backpack sprayer, crop dusters (i.e. aerial spraying), and the like. Spraying devices and or methods providing for application of the fermentation broths, fermentation broth products, fermentation products, and compositions to either one or both of the adaxial surface and/or abaxial surface can also be used. Plants and/or plant parts that are at least partially coated with any of the aforementioned compositions are also provided herein. Also provided herein are processed plant products that comprise any of the aforementioned compositions.

In certain embodiments, plants and/or plant parts are treated by applying compositions that comprise at least one of a RLN-inhibitory Methylobacterium sp., a solid substance with adherent RLN-inhibitory Methylobacterium sp., emulsions with RLN-inhibitory Methylobacterium sp. grown therein, a RLN-inhibitory cell-free culture supernatant, fraction thereof, concentrate thereof, or any combination thereof as a soil drench, soil injection, and/or in-furrow deposit. Such soil drench, soil injections, and/or in-furrow deposit applications include, but are not limited to, treatments of a single plant part or any combination of plant parts. Soil drench, soil injections and/or in-furrow deposits can be achieved with any device that will distribute the compositions to the plant and/or plant part(s) and/or to the soil that the plant or plant parts have or will contact. Useful devices include, but are not limited to, soil injectors, in-furrow applicators, and the like.

In certain embodiments, seeds are treated by exposing the seeds to compositions that comprise at least one of a RLN-inhibitory *Methylobacterium* sp., a solid substance with adherent RLN-inhibitory *Methylobacterium* sp., emulsions with RLN-inhibitory *Methylobacterium* sp. grown therein, a RLN-inhibitory cell-free culture supernatant, fraction thereof, concentrate thereof, or any combination thereof. Seeds can be treated with the compositions provided herein by methods including, but not limited to, imbibition, coating, spraying, and the like. Seed treatments can be effected with both continuous and/or a batch seed treaters. In certain embodiments, the coated seeds can be prepared by slurrying seeds with a coating composition containing at least one of a RLN-inhibitory *Methylobacterium* sp., a solid substance with adherent RLN-inhibitory *Methylobacterium* sp., emulsions with RLN-inhibitory *Methylobacterium* sp. grown therein, a RLN-inhibitory cell-free culture supernatant, fraction thereof, concentrate thereof, or any combination thereof and air drying the resulting product. Air drying can be accomplished at any temperature that is not deleterious to the seed or the *Methylobacterium*, but will typically not be greater than 30 degrees Centigrade. The proportion of coating that comprises a solid substance and RLN-inhibitory *Methylobacterium* sp. includes, but is not limited to, a range of 0.1 to 25% by weight of the seed, 0.5 to 5% by weight of the seed, and 0.5 to 2.5% by weight of seed. In certain embodiments, a solid substance used in the seed coating or treatment will have RLN-inhibitory *Methylobacterium* sp. adhered thereon. In certain embodiments, a solid substance used in the seed coating or treatment will be associated with RLN-inhibitory *Methylobacterium* sp. and will be a fermentation broth, fermentation broth product, or composition obtained by the methods provided herein. Various seed treatment compositions and methods for seed treatment disclosed in U.S. Pat. Nos. 5,106,648, 5,512,069, and 8,181,388 are incorporated herein by reference in their entireties and can be adapted for use with an active agent comprising the compositions provided herein. In certain embodiments, the composition used to treat the seed can contain agriculturally acceptable excipients that include, but are not limited to, woodflours, clays, activated carbon, diatomaceous earth, fine-grain inorganic solids, calcium carbonate and the like. Clays and inorganic solids that can be used with the fermentation broths, fermentation broth products, or compositions provided herein include, but are not limited to, calcium bentonite, kaolin, china clay, talc, perlite, mica, vermiculite, silicas, quartz powder, montmorillonite and mixtures thereof. Agriculturally acceptable adjuvants that promote sticking to the seed that can be used include, but are not limited to, polyvinyl acetates, polyvinyl acetate copolymers, hydrolyzed polyvinyl acetates, polyvinylpyrrolidone-vinyl acetate copolymer, polyvinyl alcohols, polyvinyl alcohol copolymers, polyvinyl methyl ether, polyvinyl methyl ether-maleic anhydride copolymer, waxes, latex polymers, celluloses including ethylcelluloses and methylcelluloses, hydroxy methylcelluloses, hydroxypropylcellulose, hydroxymethylpropylcelluloses, polyvinyl pyrrolidones, alginates, dextrins, malto-dextrins, polysaccharides, fats, oils, proteins, karaya gum, jaguar gum, tragacanth gum, polysaccharide gums, mucilage, gum arabics, shellacs, vinylidene chloride polymers and copolymers, soybean-based protein polymers and copolymers, lignosulfonates, acrylic copolymers, starches, polyvinylacrylates, zeins, gelatin, carboxymethylcellulose, chitosan, polyethylene oxide, acrylamide polymers and copolymers, polyhydroxyethyl acrylate, methylacrylamide monomers, alginate, ethylcellulose, polychloroprene and syrups or mixtures thereof. Other useful agriculturally acceptable adjuvants that can promote coating include, but are not limited to, polymers and copolymers of vinyl acetate, polyvinylpyrrolidone-vinyl acetate copolymer and water-soluble waxes. Various surfactants, dispersants, anticaking-agents, foam-control agents, and dyes disclosed herein and in U.S. Pat. No. 8,181,388 can be adapted for use with an active agent comprising the fermentation broths, fermentation broth products, or compositions provided herein.

Provided herein are compositions that comprise at least one of a RLN-inhibitory *Methylobacterium* sp., a solid substance with adherent RLN-inhibitory *Methylobacterium* sp., emulsions with RLN-inhibitory *Methylobacterium* sp. grown therein, a RLN-inhibitory cell-free culture supernatant, fraction thereof, concentrate thereof, or any combination thereof that provide control of RLN damage to plants, plant parts, and plants obtained therefrom relative to untreated plants, plant parts, and plants obtained therefrom that have not been exposed to the compositions. In certain embodiments, plant parts, including, but not limited to, a seed, a leaf, a fruit, a stem, a root, a tuber, a pollen grain, or a coleoptile can be treated with the compositions provided herein to inhibit of RLN growth and/or reproduction and/or reduce of RLN damage to a plant. Treatments or applications can include, but are not limited to, spraying, coating, partially coating, immersing, and/or imbibing the plant or plant parts with the compositions provided herein. In certain embodiments, a seed, a leaf, a fruit, a stem, a root, a tuber, or a coleoptile can be immersed and/or imbibed with a liquid, semi-liquid, emulsion, or slurry of a composition provided herein. Such seed immersion or imbibition can be sufficient to provide for inhibition of RLN growth and/or reductions in RLN damage in a treated plant or plant part in comparison to an untreated plant or plant part. Such inhibition of RLN growth and/or reductions in RLN damage includes, but is not limited to inhibition of RLN development and/or reproduction, disruption of RLN feeding behaviors, inhibition of motility, and/or reductions in damage to roots, tubers, or other plant parts relative to untreated plants. In certain embodiments, plant seeds can be immersed and/or imbibed for at least 1, 2, 3, 4, 5, or 6 hours. Such immersion and/or imbibition can, in certain embodiments, be conducted at temperatures that are not deleterious to the plant seed or the *Methylobacterium*. In certain embodiments, the seeds can be treated at about 15 to about 30 degrees Centigrade or at about 20 to about 25 degrees Centigrade. In certain embodiments, seed imbibition and/or immersion can be performed with gentle agitation.

Amounts of the compositions that comprise at least one of a RLN-inhibitory *Methylobacterium* sp., a solid substance with adherent RLN-inhibitory *Methylobacterium* sp., emulsions with RLN-inhibitory *Methylobacterium* sp. grown therein, a RLN-inhibitory cell-free culture supernatant, fraction thereof, concentrate thereof, or any combination thereof sufficient to provide for a reduction in RLN damage of a plant or plant part can thus be determined by measuring any or all of changes in RLN feeding behavior, RLN growth, RLN reproduction, RLN motility, numbers of recovered RLN, numbers of viable RLN, and/or the adverse effects of RLN feeding in treated plants or plant parts relative to untreated plants or plant parts. Adverse effects of RLN growth and/or reproduction in a plant that can be measured include any type of plant tissue damage or necrosis (e.g., damage of plant parts including but not limited to roots and tubers), any type of plant yield reduction, any reduction in the value of the crop plant product, and/or increases in fungal disease incidence. In certain embodiments, an RLN damage rating scale can be used to assess inhibition of RLN growth and/or reproduction and/or reductions in damage to a plant or plant part.

Compositions provided herein comprising at least one of a RLN-inhibitory *Methylobacterium* sp., a solid substance with adherent RLN-inhibitory *Methylobacterium* sp., emulsions with RLN-inhibitory *Methylobacterium* sp. grown therein, a RLN-inhibitory cell-free culture supernatant, fraction thereof, concentrate thereof, or any combination thereof are therefore expected to be useful in inhibiting RLN growth, motility, and/or reproduction and/or reducing RLN damage in a wide variety of plants, including, but not limited to: Brassica sp. (e.g., B. napus, B. rapa, B. juncea), corn, wheat, rye, rice, alfalfa, rice, rye, sorghum, millet (e.g., pearl millet (Pennisetum glaucum), proso millet (Panicum miliaceum), foxtail millet (Setaria italica), finger millet (Eleusine coracana), sunflower, safflower, soybean, tobacco, potato, peanuts, carrot, cotton, sweet potato (Ipomoea batatus), cassava, coffee, coconut, pineapple, citrus trees, cocoa, tea, banana, avocado, fig, guava, mango, olive, papaya, cashew, macadamia, almond, sugar beets, sugarcane, strawberry, oats, okra, onion, barley, tomato, lettuce, pepper, green beans, lima beans, peas, cucurbits such as cucumber, cantaloupe, and musk melon, turf, ornamentals, and conifers. Compositions provided herein are also expected to be useful in inhibiting growth and/or reducing damage caused by Pratylenchus brachyurus, Pratylenchus coffeae, P. neglectus, Pratylenchus penetrans, Pratylenchus scribneri, Pratylenchus thornei, Pratylenchus vulnus, and Pratylenchus zeae.

In certain embodiments, an amount of a composition provided herein that is sufficient to provide for inhibition of RLN damage in a plant or plant part can be a composition with RLN-inhibitory Methylobacterium sp. at a titer of at least about $1 \times 10^4$ colony-forming units per milliliter, at least about $1 \times 10^5$ colony-forming units per milliliter, at least about $1 \times 10^6$ colony-forming units per milliliter, at least about $5 \times 10^6$ colony-forming units per milliliter, at least about $1 \times 10^7$ colony-forming units per milliliter, at least about $5 \times 10^8$ colony-forming units per milliliter, at least about $1 \times 10^9$ colony-forming units per milliliter, at least about $1 \times 10^{10}$ colony-forming units per milliliter, or at least about $3 \times 10^{10}$ colony-forming units per milliliter. In certain embodiments, an amount of a composition provided herein that is sufficient to provide for inhibition of RLN growth and/or reproduction and/or reduction of RLN damage to a plant or plant part can be a composition with RLN-inhibitory Methylobacterium sp. at a titer of at least about $1 \times 10^4$ colony-forming units per milliliter, at least about $1 \times 10^5$ colony-forming units per milliliter, about least about $1 \times 10^6$ colony-forming units per milliliter, at least about $5 \times 10^6$ colony-forming units per milliliter, at least about $1 \times 10^7$ colony-forming units per milliliter, or at least about $5 \times 10^8$ colony-forming units per milliliter to at least about $6 \times 10^{10}$, $1 \times 10^{11}$, $5 \times 10^{11}$, or $1 \times 10^{12}$ colony-forming units per milliliter of a liquid or an emulsion. In certain embodiments, an amount of a composition provided herein that is sufficient to provide for inhibition of RLN growth and/or reproduction and/or reduction of RLN damage to a plant or plant part can be a fermentation broth product with a RLN-inhibitory Methylobacterium sp. titer of a solid phase of that product is at least about $1 \times 10^4$ colony-forming units per gram, at least about $1 \times 10^5$ colony-forming units per gram, at least about $1 \times 10^6$ colony-forming units per gram, at least about $5 \times 10^6$ colony-forming units per gram, at least about $1 \times 10^7$ colony-forming units per gram, or at least about $5 \times 10^8$ colony-forming units per gram to at least about $6 \times 10^{10}$ colony-forming units of Methylobacterium per gram, at least about $1 \times 10^{11}$ colony-forming units of Methylobacterium per gram, at least about $1 \times 10^{12}$ colony-forming units of Methylobacterium per gram, at least about $1 \times 10^{13}$ colony-forming units of Methylobacterium per gram, or at least about $5 \times 10^{13}$ colony-forming units of Methylobacterium per gram of the solid phase. In certain embodiments, an amount of a composition provided herein that is sufficient to provide for inhibition of RLN growth, motility, and/or reproduction and/or reduction of RLN damage to a plant or plant part can be a composition with a Methylobacterium titer of at least about $1 \times 10^6$ colony-forming units per gram, at least about $5 \times 10^6$ colony-forming units per gram, at least about $1 \times 10^7$ colony-forming units per gram, or at least about $5 \times 10^8$ colony-forming units per gram to at least about $6 \times 10^{10}$ colony-forming units of Methylobacterium per gram, at least about $1 \times 10^{11}$ colony-forming units of Methylobacterium per gram, at least about $1 \times 10^{12}$ colony-forming units of Methylobacterium per gram, at least about $1 \times 10^{13}$ colony-forming units of Methylobacterium per gram, or at least about $5 \times 10^{13}$ colony-forming units of Methylobacterium per gram of particles in the composition containing the particles that comprise a solid substance wherein a mono-culture or co-culture of RLN-inhibitory Methylobacterium sp. is adhered thereto. In certain embodiments, an amount of a composition provided herein that is sufficient to provide for inhibition of RLN growth, motility, and/or reproduction and/or reduction of RLN damage to a plant or plant part can be a composition with a Methylobacterium titer of at least about $1 \times 10^6$ colony-forming units per mL, at least about $5 \times 10^6$ colony-forming units per mL, at least about $1 \times 10^7$ colony-forming units per mL, or at least about $5 \times 10^8$ colony-forming units per mL to at least about $6 \times 10^{10}$ colony-forming units of Methylobacterium per mL in a composition comprising an emulsion wherein a mono-culture or co-culture of a RLN-inhibitory Methylobacterium sp. adhered to a solid substance is provided therein or grown therein. In certain embodiments, an amount of a composition provided herein that is sufficient to provide for inhibition of RLN growth motility, and/or reproduction and/or reduction of RLN damage to a plant or plant part can be a composition with a Methylobacterium titer of at least about $1 \times 10^6$ colony-forming units per mL, at least about $5 \times 10^6$ colony-forming units per mL, at least about $1 \times 10^7$ colony-forming units per mL, or at least about $5 \times 10^8$ colony-forming units per mL to at least about $6 \times 10^{10}$ colony-forming units of Methylobacterium per mL of in a composition comprising an emulsion wherein a mono-culture or co-culture of a RLN-inhibitory Methylobacterium sp. is provided therein or grown therein.

EXAMPLES

The following examples are included to demonstrate certain embodiments. It will be appreciated by those of skill in the art that the techniques disclosed in the following examples represent techniques determined by the Applicants to function well in the practice of the disclosure. However, those of skill in the art should, in light of the instant disclosure, appreciate that many changes can be made in the specific embodiments that are disclosed, while still obtaining like or similar results, without departing from the scope of the invention.

Example 1. Root Lesion Nematodes (RLN) in Vitro Assay

Pratylenchus penetrans (WI isolate) in all vermiform stages were purchased from the MacGuidwin Nematology Lab, University of Wisconsin-Madison. (available on the http internet site "labs.russell.wisc.edu/macguidwinlab/category/uncategorized").

The growth medium was a liquid base medium amended with a solid substance. Thus, the medium was comprised of both a liquid phase and a solid phase.

The liquid base medium was Ammonium Mineral Salts (AMS) containing peptone, glutamate as the carbon source, and diatomaceous earth as the solid substance.

To prepare this medium, three stock solutions were made as follows.

Stock solution I was made by dissolving 35 grams of anhydrous dibasic potassium phosphate and 27 grams of anhydrous monobasic potassium phosphate in a final volume of 1 liter of distilled water. Stock solution I was at a 50× concentration.

Stock solution II was made by dissolving 50 grams of magnesium sulfate heptahydrate and 25 grams of anhydrous ammonium chloride in a final volume of 1 liter of distilled water. Stock Solution II was at a 50× concentration.

Stock solution III was made by dissolving 10 grams calcium chloride dihydrate in one liter of distilled water. Stock Solution III was at 50× concentration.

Iron (II) sulfate stock solution was made by dissolving 5 g iron (II) sulfate heptahydrate in one liter of distilled water. Iron (II) sulfate stock solution was at 1000× concentration.

To prepare one liter of growth medium, 20 ml of stock solution I, 20 ml of stock solution II, 20 ml of stock solution III, 1 ml iron (II) stock solution, 10 grams of peptone, 15 grams of sodium glutamate, and 2 grams of diatomaceous earth were added to 940 ml of distilled water. The growth medium was autoclaved before use.

Single PPFM colonies were used to inoculate cultures. The cultures were grown for 4 days at 30 degrees centigrade with shaking at 200 rpm to titer of $1 \times 10^7$ to $1 \times 10^8$ CFU/ml.

Two ml of each culture was spun down at 10,000×g for 5 min, and the supernatant was passed through a 0.2 micron acrodisc syringe filter (Pall Corporation, Port Washington, N.Y.) to obtain a cell-free culture supernatant. An antibiotic solution with final concentrations of 0.025 mg/ml chlorotetracycline (Sigma-Aldrich, St. Louis, Mo.), 0.025 mg/ml chloramphenicol (Sigma-Aldrich, St. Louis, Mo.), 0.05 mg/ml Nystatin (Sigma-Aldrich, St. Louis, Mo.), and 2.5% ethanol was used to control growth of microorganisms over the course of the experiment. 2:1:1 supernatant: antibiotic solution: 200 P. penetrans nematodes in water were added to each well of a 96 well plate. Each plate was divided into 5 complete randomized blocks, with each isolate and control repeated once per block. The activity of the P. penetrans nematodes was rated after 3 days under a dissecting microscope. The rating system was 1=no movement, nematodes mostly straight; 2=some moving, curly; 3=most/all moving, curly.

The experiment was repeated twice. A linear mixed model was fitted using the "lmer" function in the lme4 package (Bates, D., Maechler, M., Bolker, B., & Walker, S. (2014). lme4: Linear mixed-effects models using Eigen and S4. R package version 1.1-7, Available on the http internet site "CRAN.R-project.org/package=lme4")) in R (R Core Team (2013). R: A language and environment for statistical computing. R Foundation for Statistical Computing, Vienna, Austria, available on the world wide web internet site "R-project.com") with random effect of experiment. P values were estimated using a normal distribution. Results are shown in Table 3.

TABLE 3

Effect of PPFM cell-free culture supernatants on RLN activity.

| Strain | Average Activity Score | Difference from Control (%) | p value |
|---|---|---|---|
| Control | 1.550 | | |
| NLS0017 | 1.500 | −3% | 0.778 |
| NLS0020 | 1.833 | 18% | 0.120 |
| NLS0021 | 1.000 | −35% | 0.002 |
| NLS0037 | 1.611 | 4% | 0.738 |
| NLS0038 | 1.100 | −29% | 0.011 |
| NLS0042 | 1.000 | −35% | 0.002 |
| NLS0934 | 1.150 | −26% | 0.024 |
| NLS0046 | 1.889 | 22% | 0.063 |
| NLS0062 | 1.200 | −23% | 0.049 |
| NLS0064 | 1.450 | −6% | 0.573 |
| NLS0065 | 1.250 | −19% | 0.091 |
| NLS0066 | 1.650 | 6% | 0.573 |

TABLE 3-continued

Effect of PPFM cell-free culture supernatants on RLN activity.

| Strain | Average Activity Score | Difference from Control (%) | p value |
|---|---|---|---|
| NLS0068 | 1.300 | −16% | 0.159 |
| NLS0069 | 1.100 | −29% | 0.011 |
| NLS0089 | 1.150 | −26% | 0.024 |

Each line in the table is the results of 5 replicates in each of two separate experiments. A linear mixed model was fitted with the random effect of experiment.

Each line in the table is the results of inverse variance meta-analysis combining the results of six independent experiments. Each strain was tested in at least three separate experiments.

Cell-free culture supernatants from strains NLS0021, NLS0038, NLS0042, NLS0934, NLS0062, NLS0069, and NLS0089 show significant decreases in activity scores for P. penetrans. Cell-free culture supernatants from strains NLS0017, NLS0037, NLS0064, and NLS0066 showed negligible effects on activity scores for P. penetrans.

Example 2. Root Lesion Nematodes (RLN) in Planta Assay

*Pratylenchus penetrans* (WI isolate) in all vermiform stages were purchased from the MacGuidwin Nematology Lab, University of Wisconsin-Madison. (available on the http internet site "labs.russell.wisc.edu/macguidwinlab/category/uncategorized").

Tomato seeds (*Solanum lycopersicum* variety "Charger" or "Sweet Olive", Johnny's Selected Seeds, Winslow, Me.) in horticubes were treated with 0.25 ml PPFM solution in water at concentration of $1 \times 10^7$ to $1 \times 10^8$ CFU/ml. This treatment simulates an in-furrow treatment applied at planting. Control seeds were treated with 0.25 ml water. Plants were grown for approximately two weeks in the greenhouse before transplanting to autoclaved 9:1 sand:soil mixture in pots. Plants were watered as needed with 2.5 g/L Jack's Professional 15-16-17 Peat-Lite Fertilizer. Plants were grown for approximately one additional week before inoculation with P. penetrans nematodes. Inoculum was prepared by diluting the purchased nematode solution to concentration of 100 nematodes/ml and adding 5 ml to holes around the roots in each pot (500 nematodes/pot total). Plants were grown approximately 6 additional weeks before harvest.

At harvest, the plant height was measured. Shoots were dried 2-3 days and dry weights were measured. Roots were extracted from the sandy soil, rinsed, and blotted dry. Root fresh and dry weights were measured. 250 ml of sandy soil was soaked in 800 ml water for approximately 1 hour with occasional stirring. The mixture was stirred and allowed to settle 1 min before decanting the water through #40 sieve. The flowthrough was stirred and allowed to settle before decanting through #170 sieve. The material caught on the #170 screen was backwashed into a clean beaker. The flowthrough was decanted through #325 sieve, and the material caught on the #325 screen was backwashed into the same clean beaker. The volume of this solution was measured and the number of nematodes in 10 microliters was counted three times under a dissecting microscope to calculate the total number of nematodes.

Each experiment contained 6 replicates per isolate arranged in 3 randomized complete blocks. The values obtained from each experiment were normalized to the average values obtained from the control plants. A linear mixed model was fitted using the "lmer" function in the lme4 package (Bates, D., Maechler, M., Bolker, B., & Walker, S. (2014). lme4: Linear mixed-effects models using Eigen and S4. R package version 1.1-7, available on the http internet site "CRAN.R-project.org/package=lme4") in R (R Core Team (2013). R: A language and environment for statistical computing. R Foundation for Statistical Computing, Vienna, Austria, available on the world wide web internet site "R-project.com") with random effect of block. An effect size and p value for each strain was calculated from results of at least three separate experiments in a total of five separate experiments using the inverse variance meta-analysis method (Lipsey, M. W., & Wilson, D. B. (2001). Practical meta-analysis. Thousand Oaks, Calif.: Sage Publications, available on the http internet site mason.gmu.edu/~dwilsonb/ma.html."). Results are shown in Table 4.

TABLE 4

Effects of seed treatments (simulated in-furrow treatment) on tomato growth parameters and RLN counts.

| Strain | Shoot Weight | | Fresh Root Weight | | Total RLN | | RLN/mg Fresh Root | |
|---|---|---|---|---|---|---|---|---|
| | Effect Size | p value | Effect Size | p value | Effect Size | p value | Effect Size | p value |
| NLS0021 | 4% | 0.326 | 14% | 0.056 | 9% | 0.218 | −13% | 0.088 |
| NLS0037 | −1% | 0.469 | −3% | 0.358 | 4% | 0.384 | 15% | 0.101 |
| NLS0038 | 11% | 0.227 | 24% | 0.064 | −10% | 0.224 | −39% | 0.001 |
| NLS0069 | 24% | 0.054 | 28% | 0.038 | 11% | 0.211 | −21% | 0.048 |

Each line in the table is the results of inverse variance meta-analysis combining the results of five independent experiments. Each strain was tested in at least three separate experiments.

Treatment with NLS0069 produces a statistically significant increase in both shoot weight and fresh root weight, while treatment with NLS0021 and NLS0038 have statistically significant increases on fresh root weight. NLS0038 and NLS0069 also significantly reduce the amount of RLN per mg root. NLS0037 does not have an inhibitory effect on the amount of RLN. These results are in agreement with the results of the RLN in vitro assay presented in Table 1.

Example 3. Field Tests

A field trial was conducted during the summer of 2016 to determine the ability of PPFMs to suppress root lesion nematode (RLN; *Pratylenchus penetrans*) on spring wheat (*Triticum aestivum* L.; var. RB07, supplied by Johnson Grain Inc.). The trial was planted on May 30, 2016 and harvested on Oct. 11, 2016. Metrics collected include: Stand, vigor at 7-days post planting, vigor at 21-days post planting, plot height at Feekes 10.5 growth stage, flowering at Feekes 10.5, lodging, yield, pre-plant nematode counts and in-season nematode counts for RLN, stunt nematode (*Tylenchorhynchus* spp.), and total plant parasitic nematodes. The experiment was designed as a randomized complete block with five treatments (Table 5) and four replications. Each experimental plot consisted of four 10-foot rows, with 50 grams of seed planted per plot. The entire experiment was surrounded by two border rows to mitigate edge effects.

Wheat seed for the trial was treated at NewLeaf Symbiotics' laboratory facilities in St. Louis, Mo. and shipped to Moccasin, Mont., where the field trial was conducted. All PPFM treatments were applied at a rate of 14 mL PPFM culture concentrate per pound of seed. PPFM culture concentrates had a concentration in the range of $1 \times 10^9$ to $1 \times 10^{10}$ colony forming units (CFUs) per mL of concentrate. A portion of treated seed was retained at the NewLeaf Symbiotic's facilities for PPFM enumeration. Enumeration confirmed that treatment was successful, with on-seed concentrations remaining at or above $1 \times 10^6$ colony forming units per seed until weeks after the treatment date.

TABLE 5

2016 Spring Wheat Lesion Nematode Trial Treatments

| Treatment Number | Treatment | Application Timing | Rate |
|---|---|---|---|
| 1 | Untreated control | N/A | N/A |
| 2 | NLS0021 | Seed treatment | 14 mL/lb |
| 3 | NLS0038 | Seed treatment | 14 mL/lb |
| 4 | NLS0066 | Seed treatment | 14 mL/lb |
| 5 | NLS0069 | Seed treatment | 14 mL/lb |

Prior to planting, root lesion and stunt nematode populations were enumerated for each repetition by collecting 4 soil cores of ~25 g wet weight and counting the number of nematodes within each core. The average count from the four cores collected per block was calculated to provide baseline estimates for root lesion, stunt, and total plant parasitic nematode populations (Table 6). Root and stunt nematode population were again enumerated after planting, at the Feekes 3 and Feekes 7 growth stages. Multiple 25 g subsamples were collected per plot and the counts in these subsamples were averaged and used to calculate number of nematodes per kg of soil within the plot (Table 7). Throughout the growing season, various data were collected, including stand, vigor, plant height, flowering, time, and yield (Table 8).

TABLE 6

2016 Spring Wheat Plant Parasitic Nematode Pre-Plant Counts

| Repetition | Root lesion/kg soil | Stunt/kg soil | Total PP[1] Nem/kg soil |
|---|---|---|---|
| Rep 1 | 274 | 704 | 978 |
| Rep 2 | 588 | 1412 | 2001 |
| Rep 3 | 2359 | 580 | 2939 |
| Rep 4 | 1056 | 313 | 1369 |
| Average | 1069 | 752 | 1822 |

[1]PP Nem = Plant Parasitic Nematode (Root lesion + stunt)

TABLE 7

2016 Spring Wheat Root Lesion Nematode Trial In-season Counts

| Treatment | Pre-Plant | Feekes 3 | Feekes 7 |
|---|---|---|---|
| UTC | 1069.00 | 2930.00 | 4300.00 A[2] |
| NLS0021 | 1069.00 | 500.00 | 2330.00 B |
| NLS0038 | 1069.00 | 2890.00 | 1980.00 B |
| NLS0066 | 1069.00 | 3110.00 | 2840.00 AB |
| NLS0069 | 1069.00 | 2070.00 | 1430.00 B |

[2]Counts followed by the same letter do not differ significantly from one-another by Fisher's LSD; No significant differences were found between counts taken at the Feekes 3 growth stage.

TABLE 8

2016 Spring Wheat Root Lesion Nematode Trial Data Summary

| Trt | DAE Stand (SEM) | 21DAE Stand (SEM) | 7DAE Vigor (SEM) | 21DAE Vigor (SEM) | Height Feekes 10.5 (SEM) | Flowering Feekes 10.5 (SEM | Yield (kg/A) (SEM) |
|---|---|---|---|---|---|---|---|
| NLS0021 | 21.38 (1.09) | 46.25 (5.13) | 8.25 (0.75) | 8.5 (0.29) | 45.6 (0.29) | 45.60 (0.29) | 205.50 (29.58) |
| NLS0038 | 24.63 (0.80) | 46.50 (2.89) | 8.25 (0.25) | 8.50 (0.50) | 44.25 (0.99) | 44.25 (0.99) | 203.85 (25.86) |
| NLS0066 | 18.50 (4.46) | 34.13 (1.84) | 7.75 (0.25) | 8.75 (0.25) | 47.25 (2.08) | 47.25 (2.08) | 230.35 (30.23) |
| NLS0069 | 20.88 (2.60) | 38.88 (1.91) | 8.00 (0.82) | 8.50 (0.29) | 44.60 (0.37) | 44.60 (0.37) | 209.45 (13.64) |
| UTC | 20.63 (3.79) | 42.13 (3.07) | 7.50 (0.29) | 9.0 (0.00) | 45.85 (1.37) | 45.85 (1.37) | 213.42 (15.57) |

Three of four PPFM treatments applied to plants in this trial, NLS0021, NLS0038, and NLS0069, significantly suppressed root lesion nematode populations in spring wheat at growth stage Feekes 7. Data were analyzed using the IMP statistical analysis software package (version 12.0; SAS Institute, Cary, N.C., 1989-2016). A mixed model was fit in the 'Fit Model' functionality with 'Repetition' as a random factor and treatment as a fixed factor. Treatment means and post-hoc means comparisons were extracted from this analysis. The finding that NLS0021, NLS0038, and NLS0069 significantly reduced root lesion nematode populations while NLS0066 did not is consistent with findings from in vitro assays reported in Example 1 and supports the positive data for isolates NLS0021, NLS038, and NLS0069 reported in Example 2. Stunt nematodes were present in the soil but their populations were not significantly affected by the PPFM treatments.

Of the four strains tested, none significantly impacted yield or other growth parameters measured. This indicates that seed treatment with PPFMs presents no deleterious effects on germination, vigor, or yield of spring wheat. The trial was planted later than is ideal for spring wheat in this region of Montana. As a result, possible benefits from PPFM application to seeds may have been masked by the late planting date.

Having illustrated and described the principles of the present disclosure, it should be apparent to persons skilled in the art that the disclosure can be modified in arrangement and detail without departing from such principles.

Although the materials and methods of this disclosure have been described in terms of various embodiments and illustrative examples, it will be apparent to those of skill in the art that variations can be applied to the materials and methods described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A method for reducing *Pratylenchus* sp. damage to a plant that comprises
    (a) planting a seed that has been treated with a composition comprising: (i) a *Methylobacterium* selected from the group consisting of NLS0021, NLS0038, NLS0042, NLS0069, NLS00934, NLS0062, and NLS0089, wherein the *Methylobacterium* strains NLS0021, NLS0038, NLS0042, NLS0069, NLS00934, NLS0062, and NLS0089 have been deposited under Agricultural Research Service Culture Collection (NRRL) Designation Nos. NRRL B-50939, NRRL B-50942, NRRL B-50932, NRRL B-50936, NRRL B-67341, NRRL B-50937, and NRRL B-50933, respectively; and wherein the *Methylobacterium* is heterologous to the seed; and (ii) an agriculturally acceptable excipient and/or an agriculturally acceptable adjuvant; and
    (b) growing the plant from said treated seed in soil in the presence of a population of *Pratylenchus* sp. nematodes, wherein *Pratylenchus* sp. damage to the plant is reduced.

2. The method of claim 1, wherein the *Methylobacterium* is present on said treated seed in an amount of at least about $1 \times 10^3$ colony forming units (CFU) of said *Methylobacterium* per treated seed.

3. The method of claim 1, wherein the composition further comprises a beneficial microorganism other than *Methylobacterium*.

4. The method of claim 3, wherein the beneficial microorganism other than *Methylobacterium* is selected from a

*Bacillus* sp., a *Pseudomonas* sp., a *Coniothyrium* sp., a *Pantoea* sp., a *Streptomyces* sp., and a *Trichoderma* sp.

5. The method of claim 1, wherein the *Methylobacterium* is: (i) NLS0021 and the seed is not a lettuce seed; (ii) NLS0038 and the seed is not a tomato seed; (iii) NLS0042 or NLS0934 and the seed is not a soybean seed; (iv) NLS0062 or NLS0069 and the seed is not a corn seed; or NLS0089 and the seed is not a broccoli seed.

6. The method of claim 1, further comprising the step of applying a composition comprising a Root-Lesion Nematode (RLN)-inhibitory *Methylobacterium* sp. isolate selected from the group consisting of *Methylobacterium* NLS0021, NLS0038, NLS0042, NLS0069, NLS00934, NLS0062, and NLS0089 to soil where the plant is growing or will be grown.

7. The method of claim 1, wherein the reduction in damage is shown by an increase in yield, shoot weight, root weight, or a combination thereof in the plant in comparison to the control plant.

8. The method of claim 1, wherein the seed is a wheat seed or tomato seed.

9. The method of claim 1, wherein the *Pratylenchus* sp. is selected from the group consisting of *Pratylenchus brachyurus, Pratylenchus coffeae, P. neglectus, Pratylenchus penetrans, Pratylenchus scribneri, Pratylenchus thornei, Pratylenchus vulnus*, and *Pratylenchus zeae*.

10. The method of claim 1, wherein the seed is selected from the group consisting of a *Brassica* sp., corn, wheat, rye, rice, alfalfa, rye, sorghum, millet, soybean, tobacco, potato, peanut, carrot, cotton, coffee, coconut, pineapple, sugar beet, strawberry, oat, barley, tomato, lettuce, pepper, pea, onion, green bean, and cucurbit seed.

11. The method of claim 1, wherein the composition further comprises a pesticide.

12. The method of claim 11, wherein the pesticide is a nematicide, a fungicide or a bacteriocide.

13. The method of claim 12, wherein the nematicide provides for inhibition of RLN growth, motility, and/or reproduction; and/or reductions in RLN-mediated plant damage.

14. The method of claim 13, wherein the nematicide is selected from the group consisting of an organophosphate, biological, and a carbamate nematicide.

15. The method of claim 1, wherein the *Methylobacterium* is present on said treated seed in an amount of at or above about $1 \times 10^6$ colony forming units (CFU) of said *Methylobacterium* per seed.

16. The method of claim 15, wherein said seed is a wheat seed.

17. The method of claim 1, wherein said population of *Pratylenchus* sp. plant parasitic nematodes in soil where said plant is grown is reduced in comparison to the population of *Pratylenchus* sp. plant parasitic nematodes in soil where a control plant is grown from a control seed that is not treated with the *Methylobacterium* and that is grown in the presence of a population of *Pratylenchus* sp. plant parasitic nematodes.

18. The method of claim 1, further comprising surveying soil in which the plant is to be grown for the presence of the *Pratylenchus* sp., wherein the treated seed is planted when *Pratylenchus* sp levels in the soil are above levels that would result in *Pratylenchus* sp. damage in a plant grown from an untreated seed.

19. The method of claim 1, wherein said composition further comprises a *Methylobacterium* selected from the group consisting of NLS0064, NLS0017, NLS0065, and NLS0068, wherein the *Methylobacterium* strains NLS0064, NLS0017, NLS0065, and NLS0068 have been deposited under Agricultural Research Service Culture Collection (NRRL) Designation Nos. NRRL B-50938, NRRL B-50931, NRRL B-50935, and NRRL B-50934, respectively.

20. The method of claim 1, wherein said *Methylobacterium* is selected from the group consisting of NLS0021, NLS0038, and NLS0069.

\* \* \* \* \*

SEQUENCE LISTING

<160> NUMBER OF SEQ ID NOS: 7

<210> SEQ ID NO 1
<211> LENGTH: 1472
<212> TYPE: DNA
<213> ORGANISM: Methylobacterium sp.

<400> SEQUENCE: 1

```
gagtttgatc ctggctcaga gcgaacgctg gcggcaggct taacacatgc aagtcgaacg      60
ggcttcttcg gaagtcagtg gcagacgggt gagtaacacg tgggaacgtg cccttcggtt     120
cggaataact cagggaaact tgagctaata ccggatacgc ccttatgggg aaaggtttac     180
tgccgaagga tcggcccgcg tctgattagc ttgttggtgg ggtaacggcc taccaaggcg     240
acgatcagta gctggtctga gaggatgatc agccacactg ggactgagac acggcccaga     300
ctcctacggg aggcagcagt ggggaatatt ggacaatggg cgcaagcctg atccagccat     360
gccgcgtgag tgatgaaggc cttagggttg taaagctctt ttgtccggga cgataatgac     420
ggtaccggaa gaataagccc cggctaactt cgtgccagca gccgcggtaa tacgaagggg     480
gctagcgttg ctcggaatca ctgggcgtaa agggcgcgta ggcggccgat taagtcgggg     540
gtgaaagcct gtggctcaac cacagaattg ccttcgatac tggttggctt gagaccggaa     600
gaggacagcg gaactgcgag tgtagaggtg aaattcgtag atattcgcaa gaacaccagt     660
```

```
ggcgaaggcg gctgtctggt ccggttctga cgctgaggcg cgaaagcgtg gggagcaaac      720
aggattagat accctggtag tccacgccgt aaacgatgaa tgccagccgt tggtctgctt      780
gcaggtcagt ggcgccgcta acgcattaag cattccgcct ggggagtacg gtcgcaagat      840
taaaactcaa aggaattgac gggggcccgc acaagcggtg gagcatgtgg tttaattcga      900
agcaacgcgc agaaccttac catcccttga catggcatgt tacctcgaga gatcggggat      960
cctcttcgga ggcgtgcaca caggtgctgc atggctgtcg tcagctcgtg tcgtgagatg     1020
ttgggttaag tcccgcaacg agcgcaaccc acgtccttag ttgccatcat tcagttgggc     1080
actctaggga gactgccggt gataagccgc gaggaaggtg tggatgacgt caagtcctca     1140
tggcccttac gggatgggct acacacgtgc tacaatggcg gtgacagtgg gacgcgaaac     1200
cgcgaggttg agcaaatccc caaaagccgt ctcagttcgg attgcactct gcaactcggg     1260
tgcatgaagg cggaatcgct agtaatcgtg gatcagcacg ccacggtgaa tacgttcccg     1320
ggccttgtac acaccgcccg tcacaccatg ggagttggtc ttacccgacg cgctgcgcc      1380 aaccgcaagg gggcaggcga ccacggtagg gtcagcgact ggggtgaagt cgtaacaagg     1440
tagccgtagg ggaacctgcg gctggatcac ct                                   1472
```

<210> SEQ ID NO 2
<211> LENGTH: 1472
<212> TYPE: DNA
<213> ORGANISM: Methylobacterium sp.

<400> SEQUENCE: 2

```
ggtgatccag ccgcaggttc ccctacggct accttgttac gacttcaccc cagtcgctga       60
ccctaccgtg gtcgcctgcc tccttgcggt tggcgcagcg ccgtcgggta agaccaactc      120
ccatggtgtg acgggcggtg tgtacaaggc ccgggaacgt attcaccgtg gcgtgctgat      180
ccacgattac tagcgattcc gccttcatgc acccgagttg cagagtgcaa tccgaactga      240
gacggttttt ggggatttgc tccacctcgc ggcttcgcgt cccactgtca ccgccattgt      300
agcacgtgtg tagcccatcc cgtaagggcc atgaggactt gacgtcatcc acaccttcct      360
cgcggcttat caccggcagt ctccctagag tgcccaactg aatgatggca actaaggacg      420
tgggttgcgc tcgttgcggg acttaaccca acatctcacg acacgagctg acgacagcca      480
tgcagcacct gtgtgcacgc tccgaagag atccccgat ctctcgaggt aacatgccat       540
gtcaagggat ggtaaggttc tgcgcgttgc ttcgaattaa accacatgct ccaccgcttg      600
tgcgggcccc cgtcaattcc tttgagtttt aatcttgcga ccgtactccc caggcggaat      660
gcttaatgcg ttagcggcgc cactgacctg caagcaggcc aacggctggc attcatcgtt      720
tacggcgtgg actaccaggg tatctaatcc tgtttgctcc ccacgctttc gcgcctcagc      780
gtcagaaccg gaccagacag ccgccttcgc cactggtgtt cttgcgaata tctacgaatt      840
tcacctctac actcgcagtt ccgctgtcct cttccggtct caagccaacc agtatcgaag      900
gcaattctgt ggttgagcca caggctttca ccccgactt aatcggccgc ctacgcgccc       960
tttacgccca gtgattccga gcaacgctag ccccttcgt attaccgcgg ctgctggcac      1020
gaagttagcc ggggcttatt cttccggtac cgtcattatc gtcccggaca aaagagcttt     1080
acaaccctaa ggccttcatc actcacgcgg catggctgga tcaggcttgc gcccattgtc     1140
caatattccc cactgctgcc tccgtagga gtctgggccg tgtctcagtc ccagtgtggc      1200
tgatcatcct ctcagaccag ctactgatcg tcgccttggt aggccgttac cccaccaaca     1260
agctaatcag acgcgggccg atccttcggc agtaaacctt tccccaaaag ggcgtatccg     1320
```

| | |
|---|---|
| gtattagctc aagtttccct gagttattcc gaaccgaagg gtacgttccc acgtgttact | 1380 |
| cacccgtctg ccactgacac ccgaaggtgc ccgttcgact tgcatgtgtt aagcctgccg | 1440 |
| ccagcgttcg ctctgagcca ggatcaaact ct | 1472 |

<210> SEQ ID NO 3
<211> LENGTH: 1472
<212> TYPE: DNA
<213> ORGANISM: Methylobacterium sp.

<400> SEQUENCE: 3

| | |
|---|---|
| gagtttgatc ctggctcaga gcgaacgctg gcggcaggct taacacatgc aagtcgaacg | 60 |
| ggcaccttcg ggtgtcagtg gcagacgggt gagtaacacg tgggaacgta cccttcggtt | 120 |
| cggaataact cagggaaact tgagctaata ccggatacgc ccttttgggg aaaggtttac | 180 |
| tgccgaagga tcggcccgcg tctgattagc ttgttggtgg ggtaacggcc taccaaggcg | 240 |
| acgatcagta gctggtctga gaggatgatc agccacactg ggactgagac acggcccaga | 300 |
| ctcctacggg aggcagcagt ggggaatatt ggacaatggg cgcaagcctg atccagccat | 360 |
| gccgcgtgag tgatgaaggc cttagggttg taaagctctt ttgtccggga cgataatgac | 420 |
| ggtaccggaa gaataagccc cggctaactt cgtgccagca gccgcggtaa tacgaagggg | 480 |
| gctagcgttg ctcggaatca ctgggcgtaa agggcgcgta ggcggccgat taagtcgggg | 540 |
| gtgaaagcct gtggctcaac cacagaattg ccttcgatac tggttggctt gagaccggaa | 600 |
| gaggacagcg gaactgcgag tgtagaggtg aaattcgtag atattcgcaa gaacaccagt | 660 |
| ggcgaaggcg gctgtctggt ccggttctga cgctgaggcg cgaaagcgtg gggagcaaac | 720 |
| aggattagat accctggtag tccacgccgt aaacgatgaa tgccagccgt tggcctgctt | 780 |
| gcaggtcagt ggcgccgcta acgcattaag cattccgcct ggggagtacg gtcgcaagat | 840 |
| taaaactcaa aggaattgac gggggcccgc acaagcggtg gagcatgtgg tttaattcga | 900 |
| agcaacgcgc agaaccttac catcccttga catggcatgt tacctcgaga gatcgggat | 960 |
| cctcttcgga ggcgtgcaca caggtgctgc atggctgtcg tcagctcgtg tcgtgagatg | 1020 |
| ttgggttaag tcccgcaacg agcgcaaccc acgtccttag ttgccatcat tcagttgggc | 1080 |
| actctaggga gactgccggt gataagccgc gaggaaggtg tggatgacgt caagtcctca | 1140 |
| tggcccttac gggatgggct acacacgtgc tacaatggcg gtgacagtgg gacgcgaagc | 1200 |
| cgcgaggtgg agcaaatccc caaaaccgt ctcagttcgg attgcactct gcaactcggg | 1260 |
| tgcatgaagg cggaatcgct agtaatcgtg gatcagcacg ccacggtgaa tacgttcccg | 1320 |
| ggccttgtac acaccgcccg tcacaccatg ggagttggtc ttacccgacg gcgctgcgcc | 1380 |
| aaccgcaagg aggcaggcga ccacggtagg gtcagcgact ggggtgaagt cgtaacaagg | 1440 |
| tagccgtagg ggaacctgcg gctggatcac ct | 1472 |

<210> SEQ ID NO 4
<211> LENGTH: 1483
<212> TYPE: DNA
<213> ORGANISM: Methylobacterium sp.

<400> SEQUENCE: 4

| | |
|---|---|
| gagtttgatc ctggctcaga gcgaacgctg gcggcaggct taacacatgc aagtcgaacg | 60 |
| caccgcaagg tgagtggcag acgggtgagt aacacgtggg aacgtgccct ccggtctggg | 120 |
| ataaccctgg gaaactaggg ctaataccgg atacgtgctt tggcagaaag gtttactgcc | 180 |

```
ggaggatcgg cccgcgtctg attagcttgt tggtggggta acggcctacc aaggcgacga    240
tcagtagctg gtctgagagg atgatcagcc acactgggac tgagacacgg cccagactcc    300
tacgggaggc agcagtgggg aatattggac aatgggcgca agcctgatcc agccatgccg    360
cgtgagtgat gacggcctta gggttgtaaa gctcttttct ccgggacgat aatgacggta    420
ccggaggaat aagccccggc taacttcgtg ccagcagccg cggtaatacg aaggggggcta   480
gcgttgctcg gaatcactgg gcgtaaaggg cgcgtaggcg cgttttaag tcggggggtga    540
aagcctgtgg ctcaaccaca gaatggcctt cgatactggg acgcttgagt atggtagagg    600
ttggtggaac tgcgagtgta gaggtgaaat tcgtagatat tcgcaagaac accggtggcg    660
aaggcggcca actggaccat tactgacgct gaggcgcgaa agcgtgggga gcaaacagga    720
ttagataccc tggtagtcca cgccgtaaac gatgaatgct agctgttggg gtgcatgcac    780
cgcagtagcg cagctaacgc attaagcatt ccgcctgggg agtacggtcg caagattaaa    840
actcaaagga attgacgggg gcccgcacaa gcggtggagc atgtggttta attcgaagca    900
acgcgcagaa ccttaccatc ctttgacatg gcgtgttact gggagagatt ccaggtcccc    960
ttcggggggcg cgcacacagg tgctgcatgg ctgtcgtcag ctcgtgtcgt gagatgttgg   1020
gttaagtccc gcaacgagcg caacccacgt ccttagttgc catcatttgg ttgggcactc   1080
tagggagact gccggtgata agccgcgagg aaggtgtgga tgacgtcaag tcctcatggc   1140
ccttacggga tgggctacac acgtgctaca atggcggtga cagtgggacg cgaaggggtg   1200
accccggagcc aatctccaaa agccgtctca gttcggattg cacgctgcaa ctcgcgtgca   1260
tgaaggcgga atcgctagta atcgtggatc agcatgccac ggtgaatacg ttcccgggcc   1320
ttgtacacac cgcccgtcac accatgggag ttggtcttac ccgacggcgc tgcgccaacc   1380
aaatcgagct tgctcgactg gaggcaggcg accacgtag gtcagcgac tggggtgaag    1440
tcgtaacaag gtagccgtag gggaacctgc ggctggatca cct                     1483

<210> SEQ ID NO 5
<211> LENGTH: 1472
<212> TYPE: DNA
<213> ORGANISM: Methylobacterium sp.

<400> SEQUENCE: 5
ggtgatccag ccgcaggttc ccctacggct accttgttac gacttcaccc cagtcgctga    60
ccctaccgtg gtcgcctgcc tccttgcggt tggcgcagcg ccgtcgggta agaccaactc   120
ccatggtgtg acgggcggtg tgtacaaggc ccgggaacgt attcaccgtg gcgtgctgat   180
ccacgattac tagcgattcc gccttcatgc acccgagttg cagagtgcaa tccgaactga   240
gacggttttt ggggatttgc tccacctcgc ggcttcgcgt cccactgtca ccgccattgt   300
agcacgtgtg tagcccatcc cgtaagggcc atgaggactt gacgtcatcc acaccttcct   360
cgcggcttat caccggcagt ctccctagag tgcccaactg aatgatggca actaaggacg   420
tgggttgcgc tcgttgcggg acttaaccca acatctcacg acacgagctg acgacagcca   480
tgcagcacct gtgtgcacgc ctccgaagag gatccccgat ctctcgaggt aacatgccat   540
gtcaagggat ggtaaggttc tgcgcgttgc ttcgaattaa accacatgct ccaccgcttg   600
tgcgggcccc cgtcaattcc tttgagtttt aatcttgcga ccgtactccc caggcggaat   660
gcttaatgcg ttagcggcgc cactgacctg caagcaggcc aacggctggc attcatcgtt   720
tacgcgtgg actaccaggg tatctaatcc tgtttgctcc ccacgctttc gcgcctcagc   780
gtcagaaccg gaccagacag ccgccttcgc cactggtgtt cttgcgaata tctacgaatt   840
```

```
tcacctctac actcgcagtt ccgctgtcct cttccggtct caagccaacc agtatcgaag      900
gcaattctgt ggttgagcca caggctttca cccccgactt aatcggccgc ctacgcgccc      960
tttacgccca gtgattccga gcaacgctag ccccttcgt attaccgcgg ctgctggcac       1020
gaagttagcc ggggcttatt cttccggtac cgtcattatc gtcccggaca aaagagcttt      1080
acaaccctaa ggccttcatc actcacgcgg catggctgga tcaggcttgc gcccattgtc      1140
caatattccc cactgctgcc tcccgtagga gtctgggccg tgtctcagtc ccagtgtggc      1200
tgatcatcct ctcagaccag ctactgatcg tcgccttggt aggccgttac cccaccaaca      1260
agctaatcag acgcgggccg atccttcggc agtaaacctt ccccaaaag gcgtatccg        1320
gtattagctc aagtttccct gagttattcc gaaccgaagg gtacgttccc acgtgttact      1380
cacccgtctg ccactgacac ccgaaggtgc ccgttcgact tgcatgtgtt aagcctgccg      1440
ccagcgttcg ctctgagcca ggatcaaact ct                                    1472

<210> SEQ ID NO 6
<211> LENGTH: 1470
<212> TYPE: DNA
<213> ORGANISM: Methylobacterium sp.

<400> SEQUENCE: 6
ggtgatccag ccgcaggttc ccctacggct accttgttac gacttcaccc cagtcgctga      60
ccctaccgtg gtcgcctgcc tccttgcggt tggcgcagcg ccgtcgggta agaccaactc      120
ccatggtgtg acgggcggtg tgtacaaggc ccgggaacgt attcaccgtg gcatgctgat      180
ccacgattac tagcgattcc gccttcatgc acccgagttg cagagtgcaa tccgaactga      240
gacggctttt ggggatttgc tcaacctcgc ggtttcgcgt cccactgtca ccgccattgt      300
agcacgtgtg tagcccatcc cgtaagggcc atgaggactt gacgtcatcc acaccttcct      360
cgcggcttat caccggcagt ctccctagag tgcccaactg aatgatgcaa ctaaggacg       420
tgggttgcgc tcgttgcggg acttaaccca acatctcacg acacgagctg acgacagcca      480
tgcagcacct gtgtgcaggt ccccgaaggg aacgaccgat ctctcggaca atcctgccat      540
gtcaagggat ggtaaggttc tgcgcgttgc ttcgaattaa accacatgct ccaccgcttg      600
tgcgggcccc cgtcaattcc tttgagtttt aatcttgcga ccgtactccc caggcggaat      660
gcttaatgcg ttagcggcgc cactgacctg caagcagacc aacggctggc attcatcgtt      720
tacggcgtgg actaccaggg tatctaatcc tgtttgctcc ccacgctttc gcgcctcagc      780
gtcagaaccg gaccagacag ccgccttcgc cactggtgtt cttgcgaata tctacgaatt      840
tcacctctac actcgcagtt ccgctgtcct cttccggtct caagctttcc agtatcgaag      900
gcaattctgt ggttgagcca caggctttca cccccgactt aaaagccgc ctacgcgccc       960
tttacgccca gtgattccga gcaacgctag ccccttcgt attaccgcgg ctgctggcac       1020
gaagttagcc ggggcttatt cttccggtac cgtcattatc gtcccggaca aaagagcttt      1080
acaaccctaa ggccttcatc actcacgcgg catggctgga tcaggcttgc gcccattgtc      1140
caatattccc cactgctgcc tcccgtagga gtctgggccg tgtctcagtc ccagtgtggc      1200
tgatcatcct ctcagaccag ctactgatcg tcgccttggt aggccgttac cccaccaact      1260
agctaatcag acgcgggccg atccttcggc agtaaacctt ccccaaaag gcgtatccg        1320
gtattagctc aagtttccct gagttattcc gaaccgaagg gcacgttccc acgtgttact      1380
cacccgtctg ccgctgaccc cgaagggccc gctcgacttg catgtgttaa gcctgccgcc      1440
```

```
agcgttcgct ctgagccagg atcaaactct                                      1470

<210> SEQ ID NO 7
<211> LENGTH: 1472
<212> TYPE: DNA
<213> ORGANISM: Methylobacterium sp.

<400> SEQUENCE: 7
gagtttgatc ctggctcaga gcgaacgctg gcggcaggct taacacatgc aagtcgaacg       60
ggcttcttcg gaagtcagtg gcagacgggt gagtaacacg tgggaacgtg cccttcggtt      120
cggaataact cagggaaact tgagctaata ccggatacgc ccttacgggg aaaggtttac      180
tgccgaagga tcggcccgcg tctgattagc ttgttggtgg ggtaacggcc taccaaggcg      240
acgatcagta gctggtctga gaggatgatc agccacactg ggactgagac acggcccaga      300
ctcctacggg aggcagcagt ggggaatatt ggacaatggg cgcaagcctg atccagccat      360
gccgcgtgag tgatgaaggc cttagggttg taaagctctt ttgtccggga cgataatgac      420
ggtaccggaa gaataagccc cggctaactt cgtgccagca gccgcggtaa tacgaagggg      480
gctagcgttg ctcggaatca ctgggcgtaa agggcgcgta ggcggccgat taagtcgggg      540
gtgaaagcct gtggctcaac cacagaattg ccttcgatac tggttggctt gagaccggaa      600
gaggacagcg gaactgcgag tgtagaggtg aaattcgtag atattcgcaa gaacaccagt      660
ggcgaaggcg gctgtctggt ccggttctga cgctgaggcg cgaaagcgtg gggagcaaac      720
aggattagat accctggtag tccacgccgt aaacgatgaa tgccagccgt tggtctgctt      780
gcaggtcagt ggcgccgcta acgcattaag cattccgcct ggggagtacg gtcgcaagat      840
taaaactcaa aggaattgac gggggcccgc acaagcggtg gagcatgtgg tttaattcga      900
agcaacgcgc agaaccttac catcccttga catggcatgt tacctcgaga gatcggggat      960
cctcttcgga ggcgtgcaca caggtgctgc atggctgtcg tcagctcgtg tcgtgagatg     1020
ttgggttaag tcccgcaacg agcgcaaccc acgtccttag ttgccatcat tcagttgggc     1080
actctaggga gactgccggt gataagccgc gaggaaggtg tggatgacgt caagtcctca     1140
tggcccttac gggatgggct acacacgtgc tacaatggcg gtgacagtgg gacgcgaaac     1200
cgcgaggttg agcaaatccc caaaagccgt ctcagttcgg attgcactct gcaactcggg     1260
tgcatgaagg cggaatcgct agtaatcgtg gatcagcacg ccacggtgaa tacgttcccg     1320
ggccttgtac acaccgcccg tcacaccatg ggagttggtc ttacccgacg gcgctgcgcc     1380
aaccgcaagg gggcaggcga ccacggtagg gtcagcgact ggggtgaagt cgtaacaagg     1440
tagccgtagg ggaacctgcg gctggatcac ct                                   1472
```